(12) United States Patent
Gutka et al.

(10) Patent No.: US 11,285,210 B2
(45) Date of Patent: Mar. 29, 2022

(54) BUFFER FORMULATIONS FOR ENHANCED ANTIBODY STABILITY

(71) Applicant: Outlook Therapeutics, Inc., Cranbury, NJ (US)

(72) Inventors: Hiten Gutka, Cranbury, NJ (US); Maria Taddei, Cranbury, NJ (US); Jessica Cheung, Cranbury, NJ (US)

(73) Assignee: Outlook Therapeutics, Inc., Monmouth Junction, NJ (US)

( * ) Notice: Subject to any disclaimer, the term of this patent is extended or adjusted under 35 U.S.C. 154(b) by 269 days.

(21) Appl. No.: 16/072,991

(22) PCT Filed: Feb. 1, 2017

(86) PCT No.: PCT/US2017/016040
§ 371 (c)(1),
(2) Date: Jul. 26, 2018

(87) PCT Pub. No.: WO2017/136433
PCT Pub. Date: Aug. 10, 2017

(65) Prior Publication Data
US 2019/0030163 A1    Jan. 31, 2019

Related U.S. Application Data

(60) Provisional application No. 62/290,654, filed on Feb. 3, 2016.

(51) Int. Cl.
| | |
|---|---|
| *A61K 39/395* | (2006.01) |
| *C07K 16/24* | (2006.01) |
| *A61K 47/12* | (2006.01) |
| *A61K 47/18* | (2017.01) |
| *A61K 47/26* | (2006.01) |
| *A61K 39/00* | (2006.01) |
| *A61K 47/02* | (2006.01) |

(52) U.S. Cl.
CPC ........ *A61K 39/39591* (2013.01); *A61K 47/12* (2013.01); *A61K 47/183* (2013.01); *A61K 47/26* (2013.01); *C07K 16/241* (2013.01); *A61K 2039/54* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,090,382 A | 7/2000 | Salfeld et al. |
| 6,258,562 B1 | 6/2001 | Salfeld et al. |
| 7,223,394 B2 | 5/2007 | Safeld et al. |
| 7,541,031 B2 | 6/2009 | Safeld et al. |
| 7,863,426 B2 | 1/2011 | Wan et al. |
| 7,919,264 B2 | 4/2011 | Maksymowych et al. |
| 7,935,808 B2 | 5/2011 | Gion et al. |
| 8,034,906 B2 | 10/2011 | Borhani et al. |
| 8,067,547 B2 | 11/2011 | Ewert et al. |
| 8,092,998 B2 | 1/2012 | Stuhlmüller et al. |
| 8,093,045 B2 | 1/2012 | Pla et al. |
| 8,187,836 B2 | 5/2012 | Hsieh et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,258,268 B2 | 9/2012 | Wu et al. |
| 8,372,400 B2 | 2/2013 | Salfeld et al. |
| 8,410,259 B2 | 4/2013 | Gion et al. |
| 8,414,894 B2 | 4/2013 | Salfeld et al. |
| 8,420,081 B2 | 4/2013 | Fraunhofer et al. |
| 8,455,219 B2 | 6/2013 | Hsieh et al. |
| 8,652,474 B2 | 2/2014 | Harris et al. |
| 8,663,945 B2 | 3/2014 | Pla et al. |
| 8,679,061 B2 | 3/2014 | Julian et al. |
| 8,715,664 B2 | 5/2014 | Hoffman et al. |
| 8,747,854 B2 | 6/2014 | Okun et al. |
| 8,753,633 B2 | 6/2014 | Salfeld et al. |
| 8,753,839 B2 | 6/2014 | Fraunhofer et al. |
| 8,795,670 B2 | 8/2014 | Krause et al. |
| 8,802,100 B2 | 8/2014 | Krause et al. |
| 8,802,101 B2 | 8/2014 | Krause et al. |
| 8,802,102 B2 | 8/2014 | Krause et al. |
| 8,808,700 B1 | 8/2014 | Hoffman et al. |
| 8,821,865 B2 | 9/2014 | Neu et al. |
| 8,846,046 B2 | 9/2014 | Kaymakcalan et al. |

(Continued)

FOREIGN PATENT DOCUMENTS

| | | |
|---|---|---|
| CN | 102078608 A | 6/2011 |
| CN | 102348979 A | 2/2012 |

(Continued)

OTHER PUBLICATIONS

Wang et al. (2007), J Pharm Sci 96(1): 1-26. (Year: 2007).*

(Continued)

*Primary Examiner* — Gary B Nickol
*Assistant Examiner* — Jegatheesan Seharaseyon
(74) *Attorney, Agent, or Firm* — Cooley LLP; Matthew Pavao

(57) ABSTRACT

The disclosure provides buffered formulations of adalimumab. The formulations comprise a buffer comprising an acetate salt, sorbitol, histidine and/or a histidine salt and optionally arginie and/or an arginine salt, and polysorbate 80. The formulations have an acidic pH, and enhance the thermal, conformational and colloidal stability of antibodies, including the adalimumab antibody.

15 Claims, 24 Drawing Sheets

Specification includes a Sequence Listing.

(56) References Cited

U.S. PATENT DOCUMENTS

| | | |
|---|---|---|
| 8,883,146 B2 | 11/2014 | Fraunhofer et al. |
| 8,883,156 B2 | 11/2014 | Wan et al. |
| 8,889,135 B2 | 11/2014 | Fischkoff et al. |
| 8,889,136 B2 | 11/2014 | Hoffman et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,373 B2 | 12/2014 | Banerjee et al. |
| 8,906,646 B2 | 12/2014 | Pla et al. |
| 8,911,737 B2 | 12/2014 | Fischkoff et al. |
| 8,911,741 B2 | 12/2014 | Krause et al. |
| 8,911,964 B2 | 12/2014 | Pla et al. |
| 8,916,153 B2 | 12/2014 | Wan et al. |
| 8,916,157 B2 | 12/2014 | Krause et al. |
| 8,916,158 B2 | 12/2014 | Krause et al. |
| 8,932,591 B2 | 1/2015 | Krause et al. |
| 8,940,305 B2 | 1/2015 | Krause et al. |
| 8,961,973 B2 | 2/2015 | Hoffman et al. |
| 8,961,974 B2 | 2/2015 | Hoffman et al. |
| 8,974,790 B2 | 3/2015 | Fischkoff et al. |
| 8,986,693 B1 | 3/2015 | Hoffman et al. |
| 8,992,926 B2 | 3/2015 | Fischkoff et al. |
| 8,999,337 B2 | 4/2015 | Medich et al. |
| 9,017,680 B2 | 4/2015 | Fischkoff et al. |
| 9,018,361 B2 | 4/2015 | Hickman et al. |
| 9,061,005 B2 | 6/2015 | Hoffman et al. |
| 9,062,106 B2 | 6/2015 | Bengea et al. |
| 9,067,990 B2 | 6/2015 | Wang et al. |
| 9,067,992 B2 | 6/2015 | Hoffman et al. |
| 9,072,668 B2 | 7/2015 | Dai et al. |
| 9,073,987 B2 | 7/2015 | Fischkoff et al. |
| 9,073,988 B2 | 7/2015 | Pla et al. |
| 9,085,618 B2 | 7/2015 | Ramasubramanyan et al. |
| 9,085,619 B2 | 7/2015 | Fraunhofer et al. |
| 9,085,620 B1 | 7/2015 | Hoffman et al. |
| 9,086,418 B2 | 7/2015 | Maksymowych et al. |
| 9,090,688 B2 | 7/2015 | Bengea et al. |
| 9,090,689 B1 | 7/2015 | Hoffman et al. |
| 9,090,867 B2 | 7/2015 | Pla et al. |
| 9,096,666 B2 | 8/2015 | Wan et al. |
| 9,102,723 B2 | 8/2015 | Wan et al. |
| 9,109,010 B2 | 8/2015 | Hickman et al. |
| 9,114,166 B2 | 8/2015 | Krause et al. |
| 9,150,645 B2 | 10/2015 | Subramanian et al. |
| 9,180,205 B2 | 11/2015 | Zeng et al. |
| 9,181,572 B2 | 11/2015 | Subramanian et al. |
| 9,187,559 B2 | 11/2015 | Hoffman et al. |
| 9,193,787 B2 | 11/2015 | Chumsae |
| 9,200,070 B2 | 12/2015 | Ramasubramanyan et al. |
| 9,220,781 B2 | 12/2015 | Krause et al. |
| 9,234,032 B2 | 1/2016 | Pla et al. |
| 9,272,041 B2 | 3/2016 | Krause et al. |
| 9,272,042 B2 | 3/2016 | Krause et al. |
| 9,273,132 B2 | 3/2016 | Wan et al. |
| 9,284,370 B1 | 3/2016 | Medich et al. |
| 9,289,497 B2 | 3/2016 | Krause et al. |
| 9,295,725 B2 | 3/2016 | Krause et al. |
| 9,302,011 B2 | 4/2016 | Krause et al. |
| 9,320,797 B2 | 4/2016 | Sloey et al. |
| 9,327,032 B2 | 5/2016 | Krause et al. |
| 9,328,165 B2 | 5/2016 | Wan et al. |
| 9,334,319 B2 | 5/2016 | Ramasubramanyan et al. |
| 9,334,320 B2 | 5/2016 | Okun et al. |
| 9,340,611 B2 | 5/2016 | Manning et al. |
| 9,340,612 B2 | 5/2016 | Manning et al. |
| 9,346,880 B2 | 5/2016 | Manning et al. |
| 9,359,434 B2 | 6/2016 | Subramanian et al. |
| 9,365,645 B1 | 6/2016 | Bengea et al. |
| 9,382,317 B2 | 7/2016 | Manning et al. |
| 9,393,304 B2 | 7/2016 | Fernandez et al. |
| 9,452,138 B2 | 9/2016 | Trollsas et al. |
| 9,669,093 B2 | 6/2017 | Medich et al. |
| 10,376,582 B2 | 8/2019 | Cini et al. |
| 10,696,735 B2 | 6/2020 | Yonan et al. |
| 2005/0221442 A1 | 10/2005 | Mehta et al. |
| 2008/0118496 A1 | 5/2008 | Medich et al. |
| 2008/0166348 A1 | 7/2008 | Kupper et al. |
| 2009/0028794 A1 | 1/2009 | Medich et al. |
| 2009/0123378 A1 | 5/2009 | Wong et al. |
| 2009/0226530 A1 | 9/2009 | Lassner et al. |
| 2010/0021451 A1 | 1/2010 | Wong |
| 2010/0111853 A1 | 5/2010 | Hickman et al. |
| 2010/0278822 A1 | 11/2010 | Fraunhofer et al. |
| 2010/0304436 A1 | 12/2010 | Chen et al. |
| 2011/0008831 A1 | 1/2011 | Emmerling et al. |
| 2011/0059079 A1 | 3/2011 | Babuka et al. |
| 2011/0076273 A1 | 3/2011 | Adler et al. |
| 2011/0171227 A1 | 7/2011 | Okun et al. |
| 2011/0312000 A1 | 12/2011 | Kobayashi et al. |
| 2012/0122076 A1 | 5/2012 | Lau et al. |
| 2013/0079272 A1 | 3/2013 | Hui et al. |
| 2013/0115224 A1 | 5/2013 | Salfeld et al. |
| 2013/0122018 A1 | 5/2013 | Salfeld et al. |
| 2013/0243764 A1 | 9/2013 | Ellis et al. |
| 2013/0330356 A1 | 12/2013 | Salfeld et al. |
| 2013/0338344 A1 | 12/2013 | Ramasubramanyan et al. |
| 2014/0141007 A1 | 5/2014 | Fraunhofer et al. |
| 2014/0141008 A1 | 5/2014 | Fraunhofer et al. |
| 2014/0170152 A1 | 6/2014 | Hsieh et al. |
| 2014/0186368 A1 | 7/2014 | Fischkoff et al. |
| 2014/0186446 A1 | 7/2014 | Trollsas et al. |
| 2014/0200332 A1 | 7/2014 | Kaymakcalan et al. |
| 2014/0248215 A1 | 9/2014 | Hoffman et al. |
| 2014/0255993 A1 | 9/2014 | Follstad et al. |
| 2014/0271633 A1 | 9/2014 | Hossler |
| 2014/0274912 A1 | 9/2014 | Prentice |
| 2014/0275486 A1 | 9/2014 | Chumsae |
| 2014/0288278 A1 | 9/2014 | Nti-Gyabaah et al. |
| 2014/0314745 A1 | 10/2014 | Rives et al. |
| 2014/0329279 A1 | 11/2014 | Wang et al. |
| 2014/0377275 A1 | 12/2014 | Neu et al. |
| 2015/0065696 A1 | 3/2015 | Wang et al. |
| 2015/0110799 A1 | 4/2015 | Ramasubramanyan et al. |
| 2015/0210735 A1 | 7/2015 | Hickman et al. |
| 2015/0246968 A1 | 9/2015 | Fischkoff et al. |
| 2015/0344564 A1 | 12/2015 | Hickman et al. |
| 2015/0361170 A1 | 12/2015 | Fraunhofer et al. |
| 2016/0017030 A1 | 1/2016 | Neu et al. |
| 2016/0046708 A1 | 2/2016 | Subramanian et al. |
| 2016/0083452 A1 | 3/2016 | Hickman et al. |
| 2016/0089495 A1 | 3/2016 | Julian et al. |
| 2016/0185849 A1 | 6/2016 | Hoffman et al. |
| 2016/0186130 A1 | 6/2016 | Pla et al. |
| 2016/0207992 A1 | 7/2016 | Bengea et al. |
| 2016/0235845 A1 | 8/2016 | Cini et al. |
| 2018/0009876 A1 | 1/2018 | Yonan et al. |
| 2019/0048070 A1 | 2/2019 | Santoro et al. |
| 2019/0161543 A1 | 5/2019 | Santoro et al. |

FOREIGN PATENT DOCUMENTS

| | | |
|---|---|---|
| CN | 105044222 A | 11/2015 |
| CN | 105779394 A | 7/2016 |
| EP | 0929578 B1 | 5/2003 |
| EP | 2081025 A1 | 7/2009 |
| EP | 2154244 | 2/2010 |
| EP | 2295071 A1 | 3/2011 |
| EP | 2324851 A1 | 5/2011 |
| EP | 2332565 A1 | 6/2011 |
| EP | 2335731 A2 | 6/2011 |
| EP | 2335732 A2 | 6/2011 |
| EP | 2338516 A2 | 6/2011 |
| EP | 1578439 B1 | 7/2011 |
| EP | 2359855 A2 | 8/2011 |
| EP | 2359856 A1 | 8/2011 |
| EP | 2361637 A1 | 8/2011 |
| EP | 2363144 A1 | 9/2011 |
| EP | 2363145 A1 | 9/2011 |
| EP | 2364731 A2 | 9/2011 |
| EP | 2371859 A2 | 10/2011 |
| EP | 1528933 B1 | 5/2012 |
| EP | 2500037 A2 | 9/2012 |
| EP | 2500413 A1 | 9/2012 |
| EP | 2500414 A1 | 9/2012 |

(56) References Cited

FOREIGN PATENT DOCUMENTS

| | | |
|---|---|---|
| EP | 2500415 A1 | 9/2012 |
| EP | 2500416 A1 | 9/2012 |
| EP | 2527425 A1 | 11/2012 |
| EP | 2532737 A1 | 12/2012 |
| EP | 1406656 B1 | 1/2013 |
| EP | 2660328 A1 | 11/2013 |
| EP | 2666472 A2 | 11/2013 |
| EP | 2666478 A2 | 11/2013 |
| EP | 2666479 A2 | 11/2013 |
| EP | 2666480 A2 | 11/2013 |
| EP | 2703010 A2 | 3/2014 |
| EP | 2708242 A2 | 3/2014 |
| EP | 2738178 A1 | 6/2014 |
| EP | 2738179 A1 | 6/2014 |
| EP | 1924287 B1 | 1/2015 |
| EP | 2946765 A1 | 11/2015 |
| EP | 2990485 A1 | 3/2016 |
| EP | 2397494 B1 | 8/2016 |
| EP | 2637690 B1 | 9/2016 |
| EP | 1737491 B1 | 11/2016 |
| EP | 2357200 B1 | 11/2016 |
| EP | 2359856 B1 | 5/2017 |
| JP | 2011-519567 A | 7/2011 |
| JP | 2014-052331 A | 3/2014 |
| JP | 2014-534423 A | 12/2014 |
| JP | 2015-527402 A | 9/2015 |
| WO | WO 92/13876 A1 | 8/1992 |
| WO | WO-1999/057134 A1 | 11/1999 |
| WO | WO-2005/089182 A2 | 9/2005 |
| WO | WO-2006/096461 A2 | 9/2006 |
| WO | WO 2006/125229 A2 | 11/2006 |
| WO | WO-2006/125821 A2 | 11/2006 |
| WO | WO 2007/050498 A2 | 5/2007 |
| WO | WO-2007/115813 A1 | 10/2007 |
| WO | WO 2008/033517 A2 | 3/2008 |
| WO | WO 2008/154543 A2 | 12/2008 |
| WO | WO 2009/073569 A2 | 6/2009 |
| WO | WO 2009/073805 A2 | 6/2009 |
| WO | WO 2009/118662 A2 | 10/2009 |
| WO | WO 2010/062896 A1 | 6/2010 |
| WO | WO 2010/129469 A1 | 11/2010 |
| WO | WO-2010/141478 A1 | 12/2010 |
| WO | WO 2010/141855 A1 | 12/2010 |
| WO | WO-2011/104381 A2 | 9/2011 |
| WO | WO 2012/041768 A1 | 4/2012 |
| WO | WO 2012/051147 A1 | 4/2012 |
| WO | WO 2013/011076 A | 1/2013 |
| WO | WO 2013/114164 A1 | 8/2013 |
| WO | WO 2013/114165 A1 | 8/2013 |
| WO | WO-2013/158279 A1 | 10/2013 |
| WO | WO 2013/186230 A1 | 12/2013 |
| WO | WO 2014/039903 A2 | 3/2014 |
| WO | WO 2014/055370 A1 | 4/2014 |
| WO | WO-2014/062535 A1 | 4/2014 |
| WO | WO-2014/099636 A1 | 6/2014 |
| WO | WO 2014/143185 A1 | 9/2014 |
| WO | WO-2014/158231 A1 | 10/2014 |
| WO | WO 2014/207763 A1 | 12/2014 |
| WO | WO 2015/051310 A2 | 4/2015 |
| WO | WO-2015/057910 A1 | 4/2015 |
| WO | WO 2015/140700 A1 | 9/2015 |
| WO | WO 2016/066688 A1 | 5/2016 |
| WO | WO-2016/118707 A1 | 7/2016 |
| WO | WO 2016/120413 A1 | 8/2016 |
| WO | WO 2017/120347 A1 | 7/2017 |
| WO | WO 2017/120359 A1 | 7/2017 |
| WO | WO 2017/136433 A1 | 8/2017 |
| WO | WO 2017/136753 A1 | 8/2017 |

OTHER PUBLICATIONS

Wang et al. (2000), Int J Pharmaceutics 203: 1-60. (Year: 2000).*
Carpenter et al. (1997), Pharm Res 14(8): 969-975, 1997 (Year: 1997).*
Fukuda et al. (2014), Pharm Res 31: 992-1001. (Year: 2014).*
Kim et al. (2016), Int J Pharmaceutics 51: 26-37. (Year: 2016).*
Allen, J.G. et al. (2016) "Facile Modulation of Antibody Fucosylation with Small Molecule Fucostatin Inhibitors and Cocrystal Structure with GDP-Mannose 4,6-Dehydratase" *ACS Chem Biol*, 11:2734-2743.
Bandyopadhyay, S. et al. (2015) "Physicochemical and functional characterization of a biosimilar adalimumab ZRC-3197" *Biosimilars*, 5:1-18.
Beck, A. et al. (Apr. 2012) "Biosimilar, Biobetter, and Next Generation Antibody Characterization by Mass Spectrometry" *Anal Chem*, 84(11):4637-4646.
Beck, A. et al. (2015) "Cutting-edge mass spectrometry characterization of originator, biosimilar and biobetter antibodies" *J Mass Spectrom*, 50:285-297.
Butler, M. et al. (2012) "Recent advances in technology supporting biopharmaceutical production from mammalian cells" *Appl Microbiol Biotechnol*, 96:885-894.
Cleland, J.L. et al. (Mar. 2001) "A specific molar ratio of stabilizer to protein is required for storage stability of a lyophilized monoclonal antibody" *J Pharma Sci*, 90(3): 310-321.
Cole, L. (Apr. 2012) "Screening optimal buffer conditions for a therapeutic antibody using Chirascan™-plus Automated Circular Dichroism" *Appl Photophysics*, p. 1-8 [online]. Retrieved from the Internet: http://www.photophysics.com/sites/default/files/documents/application_notes/4210Q244_AppNote_ACD.pdf. Retrieved on Jun. 30, 2015.
Costa, A.R. et al. (2013) "The impact of microcarrier culture optimization on the glycosylation profile of a monoclonal antibody" *SpringerPlus*, 2:25, 10 pages.
Fransson, J. et al. (Nov. 1996) "Local Tolerance of Subcutaneous Injections" *J Pharm Pharmacol*, 48:1012-1015.
Hossler, P. et al. (2015) "Cell Culture Media Supplementation of Bioflavonoids for the Targeted Reduction of Acidic Species Charge Variants on Recombinant Therapeutic Proteins" *Biotechnol Prog*, 31:1039-1052.
Imai-Nishiya, H et al. (2007) "Double knockdown of α1,6-fucosyltransferase (*FUT8*) and GDP-mannose 4,6-dehydratase (*GMD*) in antibody-producing cells: a new strategy for generating fully non-fucosylated therapeutic antibodies with enhanced ADCC" *BMC Biotechnology*, 7:84, 13 pages.
Kaiser, C. et al. (Sep. 2011) "Injection-site reactions upon Kineret (anakinra) administration: experiences and explanations" *Rheumatol International: Clinical and Experimental Investigations*, 32(2):295-299.
Kanda, Y. et al. (2007) "Establishment of a GDP-mannose 4,6-dehydratase (*GMD*) knockout host cell line: A new strategy for generating completely non-fucosylated recombinant therapeutics" *J Biotechnol*, 130:300-310.
Lapadula, G. et al. (Jan. 2014) "Adalimumab in the Treatment of Immune-Mediated Diseases" *Intl J Immunopathol Pharmacol*, 27(1):33-48.
Mori, K. et al. (2007) "Non-fucosylated therapeutic antibodies: the next generation of therapeutic antifodies" *Cytotechnology*, 55:109-114.
Rillahan, C.D. et al. (2012) "Global metabolic inhibitors of sialyl- and fucosyltransferases remodel the glycome" *Nat Chem Biol*, 8:661-668.
Rouiller, Y. et al. (2014) "Modulation of mAb Quality Attributes Using Microliter Scale Fed-Battch Cultures" *Biotechnol Prog*, 30:571-583.
Satoh, M. et al. (2006) "Non-fucosylated therapeutic antibodies as next-generation therapeutic antibodies" *Expert Opin Biol Ther*, 6(11): 1161-1173.
Serrato, J.A. et al. (2007) "Differences in the glycosylation profile of a monoclonal antibody produced by hybridomas cultured in serum-supplemented, serum-free or chemically defined media" *Biotechnol Appl Biochem*, 47:113-124.
Schmelzer, A.E. and W.M. Miller (2002) "Hyperosmotic Stress and Elevated $pCO_2$ Alter Monoclonal Antibody Charge Distribution and Monosaccharide Content" *Biotechnol Prog*, 18:346-353.
Tummala, S. et al. (2013) "Evaluation of Exogenous siRNA Addition as a Metabolic Engineering Tool for Modifying Biopharmaceuticals"

(56) References Cited

OTHER PUBLICATIONS

*Biotechnol Prog*, 29(2):415-424. NIH Public Access Author Manuscript; available in PMC Nov. 10, 2014, 19 pages.

Von Horsten, H.H. et al. (2010) "Production of non-fucosylated antibodies by co-expression of heterologous GDP-6-deoxy-D-lyxo-4-hexulose reductase" *Glycobiology*, 20(12): 1607-1618.

Wang, W. (Aug. 1999) "Instability, stabilization, and formulation of liquid protein pharmaceuticals" *Intl J Pharma*, 185(2): 129-188.

Wang, W. et al. (2007) "Antibody Structure, Instability and Formulation" *J Pharma Sci*, 96(1): 1-26.

Xie, P. et al. (2016) "Elucidating the effects of pH shift on IgG1 monoglonal antibody acidic charge variant levels in Chinese hamster ovary cell cultures" *Appl Microbiol Biotechnol*, 100:10343-10353.

Yamane-Ohnuki, N. and M. Satoh (2009) "Production of therapeutic antibodies with controlled fucosylation" *mAbs*, 1(3):230-236.

Zhang, X. et al. (2015) "Culture temperature modulates monoclonal antibody charge variation distribution in Chinese hamster ovary cell cultures" *Biotechnol Lett*, 37:2151-2157.

Zhou, Q. et al. (Feb. 15, 2008) "Development of a simple and rapid method for producing non-fucosylated oligomannose containing antibodies with increased effector function" *Biotechnol Bioeng*, 99(3):652-665.

GE Healthcare. (2004). "Ion Exchange Chromatography and chromatofocusing, Principles and Methods." pp. 1-170, copyright 2004-2016.

Van Reis et al. (2007). "Bioprocess membrane technology." J Membrane Science. 297: 16-50.

Du, Y. et al. (2012) "Chromatographic analysis of the acidic and basic species of recombinant monoclonal antibodies" mAbs, 4(5):578-585.

Kawasaki, Nana and Akiko Ishii (Sep. 2012) "Kotai-iyakuhin no Baio-Kouzokuhin no Syorai Tenbou (Japanese) (Future outlook for biosimilars of antibody preparations)" Rinsho to Biseibutsu (Clinical and Microorganisms), vol. 39, No. 5, p. 459-465, with English machine translation, 10 pages.

Matsuda, Rieko (1996) "Acids and Bases-Bronsted Setsu wo chushin ni (Japanese) (Focusing on the Bases-Bronsted theory)" Kagaku to Kyouiku (Chemistry & Education). The Chemical Society of Japan, vol. 44, No. 1, p. 44-47, with machine translation, 6 pages.

Becker et al. (2003). "Fucose: biosynthesis and biological function in mammals." Glycobiology. 13(7):41R-53R.

Da Silva et al. (2014). "Target-directed development and preclinical characterization of the proposed biosimilar rituximab GP2013." Leukemia & lymphoma. 55(7):1609-17.

Decision T 1784/15 of the Board of Appeal of the European Patent Office.

Freimoser-Grundschober et al. (2020). "Fc?RIIIa chromatography to enrich a-fucosylated glycoforms and assess the potency of glycoengineered therapeutic antibodies." Journal of Chromatography A. 1610:460554.

Friend et al. (1999). "Phase I Study of An Engineered Aglycosylated Humanized Cd3 Antibody in Renal Transplant Rejection1." Transplantation. 68(11):1632-7.

Khattak et al. (2009). "Feed Development for Fed-Batch CHO Production Process by Semisteady State Analysis." Biotechnol. Prag. 26(3): 797-804, 2010; available online Dec. 11, 2009.

Konno et al. (2012). "Fucose content of monoclonal antibodies can be controlled by culture medium osmolality for high antibody-dependent cellular cytotoxicity." Cytotechnology. 64(3):249-65.

Rosenlocher et al. (2015). "Applying Acylated Fucose Analogues to Metabolic Glycoengineering." Bioengineering. 2, 213-234. doi:10.3390/bioengineering2040213.

Shields et al. (2002). "Lack of fucose on human IgG1 N-linked oligosaccharide improves binding to human Fc?RIII and antibody-dependent cellular toxicity." Journal of Biological Chemistry. 277(30):26733-40.

Song et al. (2013). "Inhibition of tumor growth in a mouse xenograft model by the humanized anti-HGF monoclonal antibody YYB-101 produced in a large-scale CHO cell culture." Journal of microbiology and biotechnology. 23(9): 1327-38.

Yamane-Ohnuki et al. (2004). "Establishment of FUT8 knockout Chinese hamster ovary cells: An ideal host cell line for producing completely defucosylated antibodies with enhanced antibody? dependent cellular cytotoxicity." Biotechnology and bioengineering. 87(5):614-22.

* cited by examiner

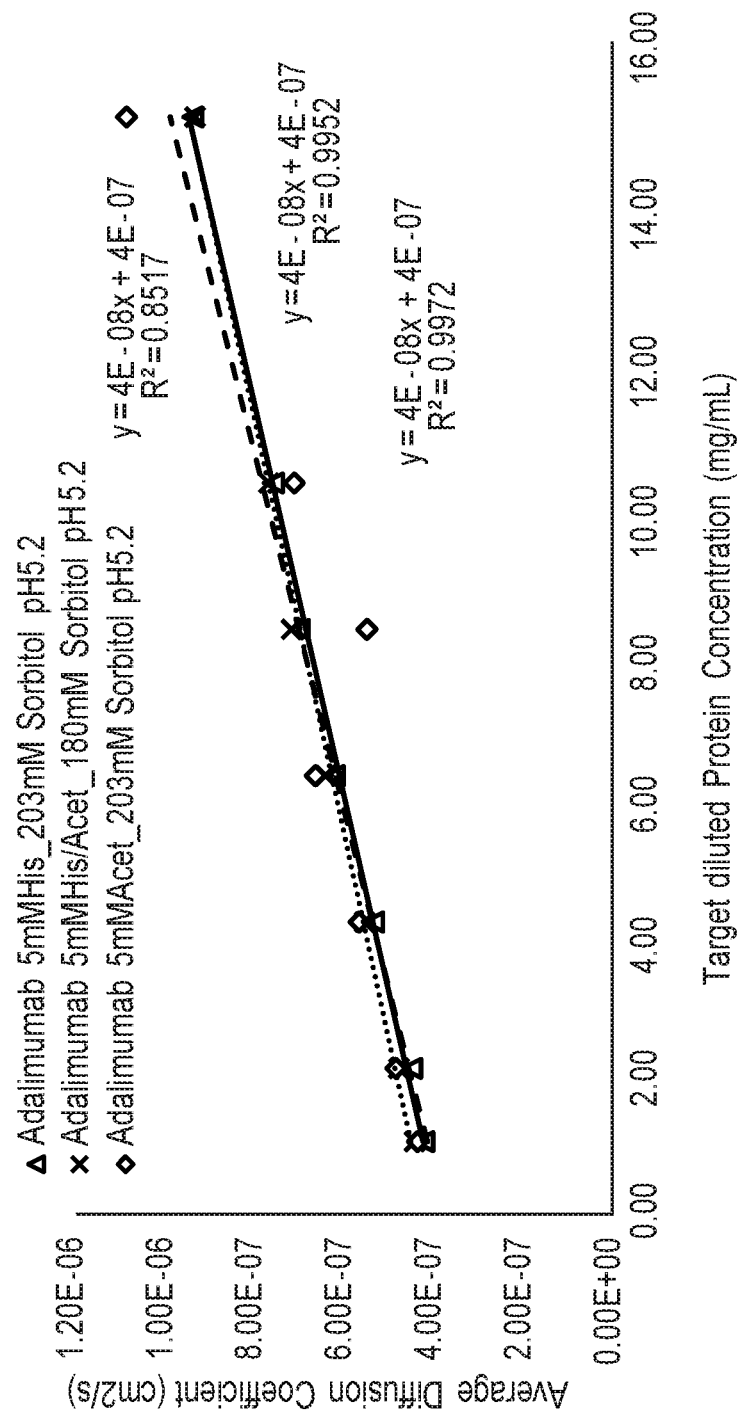

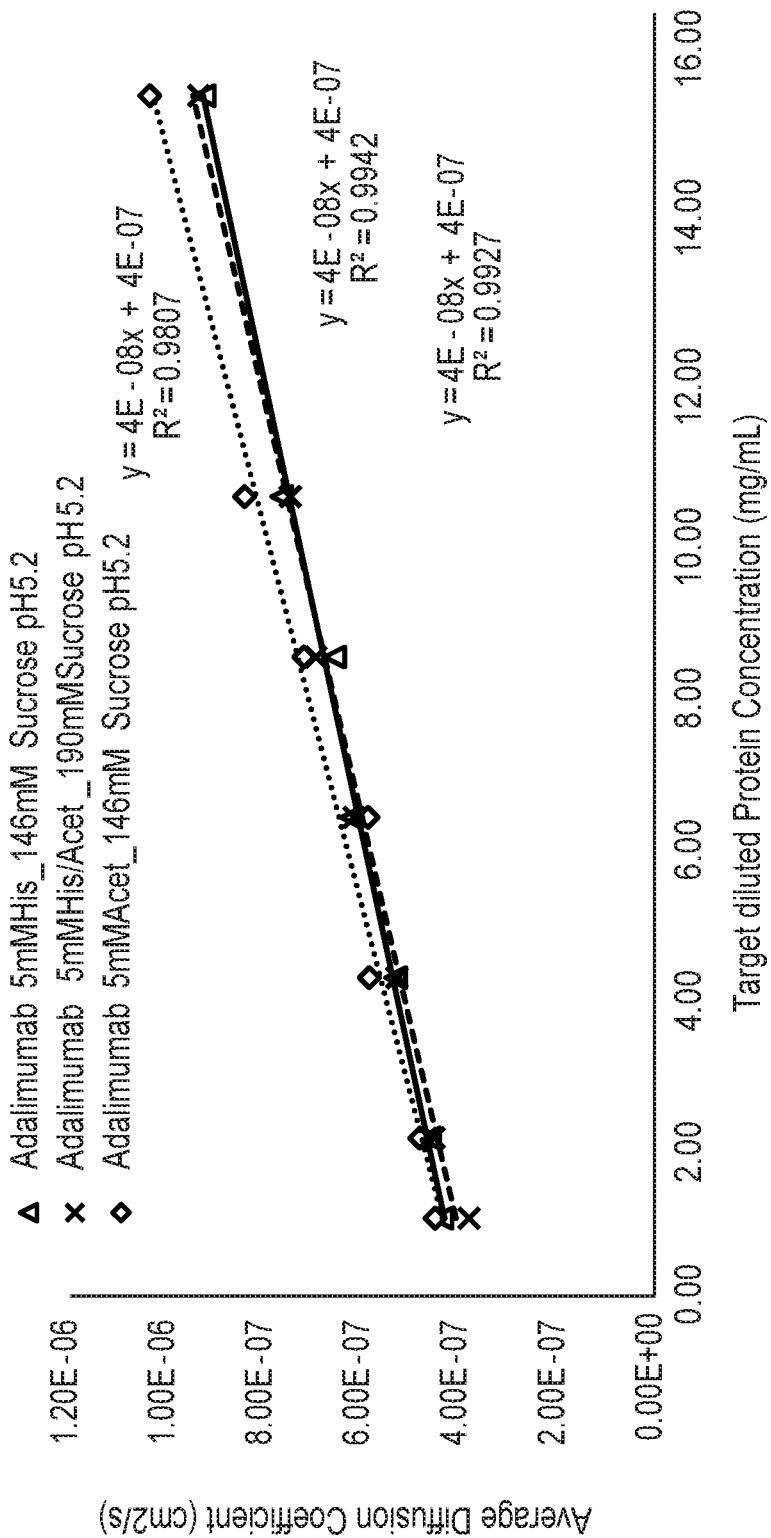

BUFFER FORMULATIONS FOR ENHANCED ANTIBODY STABILITY

RELATED APPLICATIONS

This application is a National Stage Application, filed under 35 U.S.C. 371, of International Application No. PCT/US2017/016040, filed on Feb. 1, 2017, which claims priority to U.S. Application No. 62/290,654, filed Feb. 3, 2016, the contents of each of these applications is incorporated by reference in its entirety.

INCORPORATION OF SEQUENCE LISTING

The contents of the text file named "ONBI-006N01USSequence-Listing.txt," which was created on Jul. 25, 2018 and is 12.3 KB in size, are hereby incorporated by reference in their entirety.

FIELD OF THE DISCLOSURE

The disclosure relates generally to the field of antibody formulation chemistry. More particularly, the disclosure relates to buffered formulations for antibody storage, which enhance the thermal stability, conformational and colloidal stability of the antibody, thereby enhancing long term storage of the antibody.

BACKGROUND

Various publications, including patents, published applications, accession numbers, technical articles and scholarly articles are cited throughout the specification. Each of these cited publications is incorporated by reference herein, in its entirety and for all purposes.

As part of the Biologics Price Competition and Innovation Act (BPCIA), a biological drug product (produced in or derived from living organisms) may be demonstrated to be "biosimilar" if data show that, among other things, the product is "highly similar" to an approved biological product. The biosimilar product should retain at least the biologic function and treatment efficacy of the U.S. Food and Drug Agency-approved biological product. The biosimilar product may be formulated differently, however, from the approved biological product. The formulation may improve stability and shelf storage of the biologic drug product, and may also improve the efficacy in treating a particular disease or condition. The formulation may also improve other aspects of administration, including a reduction in patient discomfort or other untoward effects that a patient may experience upon administration of the approved biological product.

Antibody molecules may be used as biological drugs, and many such antibodies are approved for use in human beings. Antibody molecules may be produced as a biosimilar, and reformulated accordingly. There remains a need in the art for high-quality antibody biosimilars.

SUMMARY

The disclosure features buffered antibody formulations (i.e., compositions of the disclosure), comprising (a) an antibody. The antibody may specifically bind to tumor necrosis factor alpha. The antibody may comprise a heavy chain comprising the amino acid sequence EVQLVESGG-GLVQPGRSLRLSCAASGFTFDDYAMHWVRQAPGK-GLEWVS AITWNSGHIDYADSVEGRFTISRDNAKNS-LYLQMNSLRAEDTAVYYCAKVSYLSTAS SLDYWGQGTLVTVSSASTKGPSVFPLAPSSKST-SGGTAALGCLVKDYFPEPVTVSWN SGALT-SGVHTFPAVLQSSGLYS-LSSVVTVPSSSLGTQTYICNVNHKPSNTKVDKKVEP KSCDKTHTCPPCPAPELLGGPSVFLFPPKPKDTLMIS-RTPEVTCVVVDVSHEDPEVKF NWYVDGVEVHNAKTKPREEQYN-STYRVVSVLTVLHQDWLNGKEYKCKVSNKALP APIEKTISKAKGQPREPQVYTLPPSRDELTKNQVSLT-CLVKGFYPSDIAVEWESNGQP ENNYKTTPPVLDSDGSFFLYSK-LTVDKSRWQQGNVFSCSVMHEALHNHYTQKSLSL SPGK (SEQ ID NO: 1) and a light chain comprising the amino acid sequence DIQMTQSP SSLSASVGDRVTIT-CRASQGIRNYLAWYQQKPGKAPKLLI-YAASTLQSGVPSRFSGSG SGTDFTLTISSLQPED-VATYYCQRYNRAPYTFGQGTKVEIKRTVAAPSVFIFP PSDEQL KSGTASVVCLLNNFYPREAKVQWKVD-NALQSGNSQESVTEQDSKDSTYSLSSTLTLS KADYEKHKVYACEVTHQGLSSPVTKSFNRGEC (SEQ ID NO: 2).

In certain embodiments, the heavy chain of the antibody comprises a variable region comprising the amino acid sequence EVQLVESGGGLVQPGRSLRLSCAASGFTFD-DYAM HWVRQAPGKGLEWVSAITWNSGHIDYADS-VEGRFTISRDNAKNSLYLQMNSLRAED TAVYY-CAKVSYLSTASSLDYWGQGTLVTVSS (SEQ ID NO: 3), a first constant domain (CH1 domain) comprising the amino acid sequence ASTKGPSVFPLAPSSKSTSGGTAAL GCLVKDYFPEPVTVSWNSGALTSGVHTFPAVLQSSG-LYSLSSVVTVPSSSLGTQTYIC NVNHKPSNTKVDKKV (SEQ ID NO: 4), a hinge region comprising the amino acid sequence EPKSCDKTHTCP (SEQ ID NO: 5), a second constant domain (CH2 domain) comprising the amino acid sequence PCPA-PELLGGPSVFLFPPKPKDTLMISRTPEVTC VVVDVSHEDPEVKFNWYVDGVEVHNAKTKPRE-EQYNSTYRVVSVLTVLHQDWLN GKEYK (SEQ ID NO: 6), and a third constant domain (CH3 domain) comprising the amino acid sequence CKVSNKALPA-PIEKTISKAKGQPREPQVYTLPPSRDELTKNQVSLTCL VKGFYPSDIAVEWESNGQPEN-NYKTTPPVLDSDGSFFLYSKLTVDKSRWQQGNVFS CSVMHEALHNHYTQKSLSLSPGK (SEQ ID NO: 7).

In certain embodiments, the light chain of the antibody comprises a variable region comprising the amino acid sequence DIQMTQSPSSLSASVGDRVTITCRASQGIR-NYL AWYQQKPGKAPKLLI-YAASTLQSGVPSRFSGSGSGTDFTLTISSLQPED-VATYYCQR YNRAPYTFGQGTKVEIKR (SEQ ID NO: 8) and a constant region comprising the amino acid sequence TVAAPSVFIFPPSDEQLKSGTASVVCLLNNFY-PREAKVQWKVDNALQ SGNSQESVTEQDSKDSTYS-LSSTLTLSKADYEKHKVYACE-VTHQGLSSPVTKSFNRG EC (SEQ ID NO: 9).

In certain embodiments, the antibody may comprise a variable heavy chain comprising the amino acid sequence EVQLVESGGGLVQPGRSLRLSCAASGFTFDDYAM HWVRQAPGKGLEWVSAITWNSGHIDYADSVEG-RFTISRDNAKNSLYLQMNSLRAED TAVYYCAKV-SYLSTASSLDYWGQGTLVTVSS (SEQ ID NO: 3) and a variable light chain comprising the amino acid sequence DIQMTQSPSSLSASVGDRVTITCRASQGIR NYLAWYQQKPGKAPKLLI-

YAASTLQSGVPSRFSGSGSGTDFTLTISSLQPED-
VATYYC QRYNRAPYTFGQGTKVEIKR (SEQ ID NO: 8).

The formulation (i.e., composition of the disclosure), in addition to the antibody, comprises (b) an aqueous buffer comprising from about 10 mM to about 30 mM of acetate or an acetate salt, preferably sodium acetate trihydrate, from about 15 mM to about 20 mM of histidine and/or a histidine salt and from about 0 mM to about 30 mM of arginine, from about 200 mM to about 206 mM of sorbitol, and (c) about 0.07% (v/v) to about 0.15% (v/v) of a non-ionic surfactant such as polysorbate 80. The buffered antibody formulation has a pH of from about 5.1 to about 5.3, preferably about 5.2.

The disclosure provides a buffered antibody formulation, comprising (a) an antibody comprising a heavy chain comprising the amino acid sequence of SEQ ID NO: 1 and a light chain comprising the amino acid sequence of SEQ ID NO: 2; (b) a buffer comprising (1) from about 1 mM to about 30 mM of an acetate salt, (2) from about 10 mM to about 30 mM of histidine and/or a histidine salt, (3) about 201 mM to about 205 mM of sorbitol, and (c) about 0.08% (v/v) to about 0.12% (v/v) of polysorbate 80, wherein the antibody formulation has a pH of from about 5.1 to about 5.3. In certain embodiments, the buffer of (b) further comprises from about 0.1 to about 30 mM of arginine and/or an arginine salt. In certain embodiments, the acetate salt comprises sodium acetate trihydrate. In certain embodiments, the wherein the pH is about 5.2. In certain embodiments, the wherein the pH is about 5.2. In certain embodiments, the formulation does not comprise NaCl, a citrate, or a phosphate.

In some aspects, the formulation comprises from about 30 mg to about 70 mg of the antibody. In some preferred aspects, the formulation comprises from about 35 mg to about 65 mg of the antibody. In some preferred aspects, the formulation comprises from about 47 mg to about 53 mg of the antibody. In some preferred aspects, the formulation comprises about 50 mg of the antibody.

The buffer may comprise from about 1 mM to about 30 mM of the acetate salt. In some embodiments, the buffer comprises from about 10 mM to about 30 mM of the acetate salt. In some embodiments, the buffer comprises from about 15 mM to about 25 mM of the acetate salt. In some embodiments, the buffer comprises from about 20 mM of the acetate salt. In some embodiments, the buffer comprises from about 1 mM of the acetate salt. In some embodiments, the acetate salt comprises sodium acetate trihydrate.

The buffer may comprise from about 0.8 mM to about 1.2 mM of sodium acetate trihydrate, or from about 0.9 mM to about 1.1 mM of sodium acetate trihydrate, or about 1 mM of sodium acetate trihydrate.

The buffer may comprise from about 10 mM to about 30 mM of histidine or a histidine salt. In certain embodiments, the buffer may comprise from about 15 mM to about 25 mM of histidine or a histidine salt. In certain embodiments, the buffer may comprise from about 20 mM of histidine or a histidine salt. In certain embodiments, the histidine salt comprises L-histidine monohydrochloride monohydrate.

The buffer may comprise from about 10 mM to about 30 mM of L-histidine and L-histidine monohydrochloride monohydrate or about from about 10 mM to about 30 mM of L-histidine and L-histidine monohydrochloride monohydrate.

The buffer may comprise from about 0.1 mM to about 30 mM of arginine or an arginine salt. In certain embodiments, the buffer may comprise from about 10 mM to about 30 mM of arginine or an arginine salt. In certain embodiments, the buffer may comprise from about 18 mM to about 20 mM of arginine or an arginine salt. The buffer may comprise from about 19 mM of arginine or an arginine salt.

The buffer may comprise from about 201 mM to about 205 mM of sorbitol, or from about 202 mM to about 204 mM of sorbitol, or about 203 mM of sorbitol. The buffer is preferably substantially free or free of sodium chloride.

The buffered antibody formulation includes a non-ionic surfactant, which preferably is polysorbate 80. In some aspects, the formulation comprises from about 0.08% (v/v) to about 0.12% (v/v) of polysorbate 80. In some aspects, the formulation comprises from about 0.09% (v/v) to about 0.11% (v/v) of polysorbate 80. In some aspects, the formulation comprises about 0.1% (v/v) of polysorbate 80.

In a detailed aspect, a buffered antibody formulation comprises (a) about 30 mg to about 70 mg of an antibody comprising a heavy chain comprising the amino acid sequence of SEQ ID NO: 1 and a light chain comprising the amino acid sequence of SEQ ID NO: 2, (b) an aqueous buffer comprising about 1 mM of an acetate salt, preferably sodium acetate trihydrate, from about 10 mM to about 30 mM of histidine and from about 0 mM to about 30 mM of arginine, about 203 mM of sorbitol, and (c) about 0.1% (by volume) of polysorbate 80. The buffered antibody formulation has a pH of from about 5.1 to about 5.3, preferably about 5.2. In some preferred aspects, the formulation comprises from about 35 mg to about 45 mg of the antibody. In some preferred aspects, the formulation comprises from about 37 mg to about 43 mg of the antibody. In some preferred aspects, the formulation comprises about 40 mg of the antibody.

The buffered antibody formulations may be used as a medicament, and may be used in methods of treatment. For example, the buffered antibody formulations may be for use in the treatment of arthritis. In some aspects, the buffered antibody formulations may be for use in the treatment of Rheumatoid Arthritis, or Juvenile Idiopathic Arthritis, or Psoriatic Arthritis. In some aspects, the buffered antibody formulations may be for use in the treatment of Ankylosing Spondylitis. In some aspects, the buffered antibody formulations may be for use in the treatment of Crohn's Disease. In some aspects, the buffered antibody formulations may be for use in the treatment of Ulcerative Colitis. In some aspects, the buffered antibody formulations may be for use in the treatment of Plaque Psoriasis.

The methods of treatment include methods for treating arthritis, including Rheumatoid Arthritis, Juvenile Idiopathic Arthritis, and Psoriatic Arthritis. The methods of treatment also include methods for treating Ankylosing Spondylitis, methods for treating Crohn's Disease, methods for treating Plaque Psoriasis, and methods for treating Ulcerative Colitis.

In some aspects, methods of treatment comprise administering to an arthritis patient, including a Rheumatoid Arthritis, Juvenile Idiopathic Arthritis, or Psoriatic Arthritis, an amount of the buffered antibody formulations described or exemplified herein effective to treat the arthritis in the patient. In some aspects, methods of treatment comprise administering to an Ankylosing Spondylitis patient an amount of the buffered antibody formulations described or exemplified herein effective to treat the Ankylosing Spondylitis in the patient. In some aspects, methods of treatment comprise administering to a Crohn's Disease patient an amount of the buffered antibody formulations described or exemplified herein effective to treat the Crohn's Disease in the patient. In some aspects, methods of treatment comprise administering to an Ulcerative Colitis patient an amount of the buffered antibody formulations described or exemplified herein effective to treat the Ulcerative Colitis in the patient. In some aspects, methods of treatment comprise administering to a Plaque Psoriasis patient an amount of the buffered antibody formulations described or exemplified herein effective to treat the Plaque Psoriasis in the patient. The buffered antibody formulations are preferably administered subcutaneously to the patient, for example, by subcutaneous injection. The patient preferably is a human being.

The disclosure also provides kits, which may be used, for example, in accordance with the methods of treatment. Thus, for example, the kits generally comprise any of the buffered antibody formulations described or exemplified herein and instructions for using the formulation in a method of treatment. The method of treatment may be a method for treating arthritis. The method of treatment may be a method for treating Rheumatoid Arthritis. The method of treatment may be a method for treating Juvenile Idiopathic Arthritis. The method of treatment may be a method for treating Psoriatic Arthritis. The method of treatment may be a method for treating Ankylosing Spondylitis. The method of treatment may be a method for treating Crohn's Disease. The method of treatment may be a method for treating Ulcerative Colitis. The method of treatment may be a method for treating Plaque Psoriasis. The kits may include a device for administering the antibody formulation to a patient. The device may comprise a syringe and a needle. The device may comprise a catheter.

BRIEF DESCRIPTION OF THE DRAWINGS

FIG. 23 is a graph depicting the colloidal stability of Adalimumab in a Histidine-acetate compared to a histidine buffer or an acetate buffer. All buffers include sorbitol as a stabilizer. The slope for line plots of all 3 buffer types is identical and the $R^2$ value of each plot is greater than or equal to about 0.9.

FIG. 24 is a graph depicting the colloidal stability of Adalimumab in a Histidine-acetate compared to a histidine buffer or an acetate buffer. All buffers include sucrose as a stabilizer. The slope for line plots of all 3 buffer types is identical and the $R^2$ value of each plot is greater than or equal to about 0.9.

DETAILED DESCRIPTION

Figure 1:
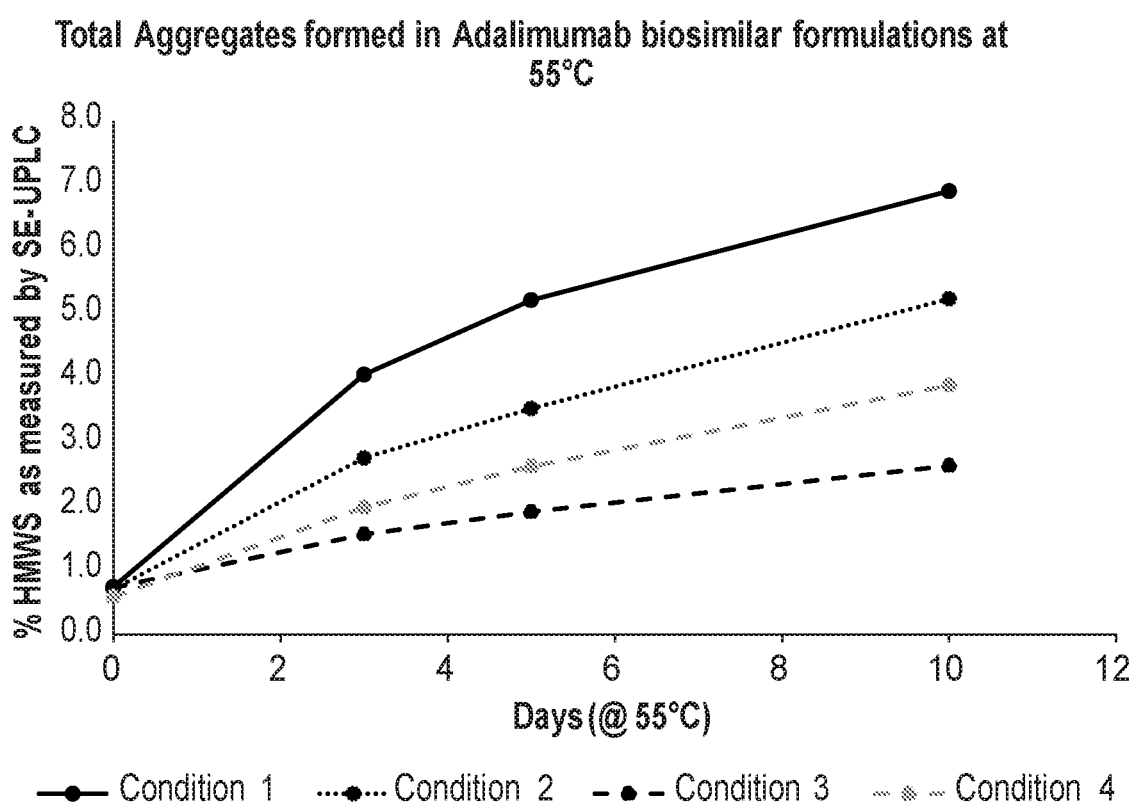
FIG. 1 is an SE-UPLC % high molecular weight species (HMWS) micrograph showing trends in aggregation in adalimumab formulations at 55° C. for 10 days.

Various terms relating to aspects of the present disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

As used herein, the terms "comprising," "having," and "including" encompass the more restrictive terms "consisting essentially of" and "consisting of."

The terms subject and patient are used interchangeably, and include any animal. Subjects include mammals, including companion and farm mammals, as well as rodents, including mice, rabbits, and rats, and other rodents. Non-human primates preferred subjects. Human beings are highly preferred subjects.

It has been observed in accordance with the disclosure that formulations of ONS-3010, which specifically binds to tumor necrosis factor alpha, can be buffered with histidine (and optionally arginine) amino acids and an acetate, while minimizing sodium chloride, with the buffers enhancing the thermal and colloidal stability of the antibody, even more so than formulations of adalimumab currently approved for patient use. It was observed that there is a fine balance in establishing and maintaining an acidic pH of about 5.2 with the appropriate salts and buffer components. It was observed, for example, that high levels of salt may induce aggregation and degradation, which could be improved by lowering the salt level. Accordingly, the disclosure features buffered formulations for antibodies, which formulations include an aqueous carrier comprising buffer comprising histidine (and optionally arginine) amino acids and an acetate, as well as mannitol and a non-ionic surfactant, but with minimal sodium chloride.

In some preferred aspects, the antibody specifically binds to an epitope on tumor necrosis factor alpha, and the epitope may be linear or conformational. In some preferred aspects, the antibody comprises a heavy chain comprising the amino acid sequence of SEQ ID NO: 1. In some preferred aspects, the antibody comprises a light chain comprising the amino acid sequence of SEQ ID NO: 2. Preferably, the antibody comprises a heavy chain constant domain and/or a light chain constant domain. In highly preferred aspects, the antibody comprises a heavy chain comprising the amino acid sequence of SEQ ID NO: 1 and a light chain comprising the amino acid sequence of SEQ ID NO: 2, an example of which is ONS-3010. The heavy and light chain amino acid sequences of the antibody may comprise those of U.S. Pat. No. 6,090,382.

Preferably, the antibody is a full length antibody, comprising both variable and constant regions, although in some aspects, the antibody may comprise a derivative or fragment or portion of a full-length antibody that retains the antigen-binding specificity, and also preferably retains most or all of the affinity, of the full length antibody molecule. The antibody may comprise post-translational modifications (PTMs) or moieties, which may impact antibody activity or stability. The antibody may be methylated, acetylated, glycosylated, sulfated, phosphorylated, carboxylated, and/or amidated, and may comprise other moieties that are well known in the art. Common PTMs for ONS-3010 include N-glycosylation, C-terminal variants (e.g., cleavage of lysine, proline amidation), N-terminal pyro-E formation, oxidation, isomerization, deamidation, succinimide formation, mannosylation, K98 glycation, and fragmentation. Moieties include any chemical group or combinations of groups commonly found on immunoglobulin molecules in nature, or otherwise added to antibodies by recombinant expression systems, including prokaryotic and eukaryotic expression systems.

The formulation preferably comprises a therapeutically effective amount of an antibody. The antibody may be any antibody compatible with the aqueous buffer formulation. A preferred antibody comprises a heavy chain having the amino acid sequence of SEQ ID NO: 1 and a light chain having the amino acid sequence of SEQ ID NO: 2. A therapeutically effective amount may vary, depending on the disease or condition being treated upon administration of the antibody, and/or depending on the characteristics of the subject to which the antibody is administered, such as age, gender, height, weight, state of advancement or stage of the disease or condition, the number and efficacy of previous administrations, other therapeutic agents administered to the subject, and other characteristics that are known to the practitioner or that would otherwise be taken into account in determining appropriate dosing. Preferably, a therapeutically effective amount is an amount that is effective to treat Rheumatoid Arthritis. In some preferred aspects, a therapeutically effective amount is an amount that is effective to treat Juvenile Idiopathic Arthritis, Psoriatic Arthritis, Ankylosing Spondylitis, Crohn's Disease, Plaque Psoriasis, Ulcerative Colitis, Inflammatory Bowel Disease, Hidradenitis Suppurativa, or Refractory Asthma.

The formulation may comprise from about 10 mg to about 70 mg of the antibody. In some aspects, the formulation comprises from about 20 mg to about 60 mg of the antibody. In some aspects, the formulation comprises from about 30 mg to about 50 mg of the antibody. In some aspects, the formulation comprises from about 35 mg to about 45 mg of the antibody. In some aspects, the formulation comprises from about 37 mg to about 43 mg of the antibody. In some aspects, the formulation comprises from about 38 mg to about 42 mg of the antibody. In some aspects, the formulation comprises from about 39 mg to about 41 mg of the antibody. In some aspects, the formulation comprises from about 30 mg to about 60 mg of the antibody. In some aspects, the formulation comprises from about 35 mg to about 55 mg of the antibody. In some aspects, the formulation comprises from about 40 mg to about 60 mg of the antibody. These ranges include the lower and upper amounts that define the range. In some aspects, the formulation comprises about 40 mg of the antibody.

The antibody is preferably formulated with a buffered aqueous carrier, and the carrier preferably comprises water. The buffered antibody formulation is preferably in liquid form, and more preferably in liquid form suitable for subcutaneous administration. Thus, the amount of water in the buffered formulation may vary in accordance with the desired volume of the injectable bolus. The buffer comprises sodium acetate trihydrate, histidine and/or a histidine salt (and optionally arginine and/or an arginine salt), mannitol, sodium chloride, and a non-ionic surfactant, and maintains the antibody formulation at an acidic pH. Prefer the buffer is a histidine acetate buffer. When stored in the buffered formulation, the antibody is shelf-stable under normal storage conditions.

The buffer may comprise from about 1.0 mM to about 30 mM of an acetate salt. In some aspects, the buffer may comprise from about 10 mM to about 30 mM of an acetate salt. In some aspects, the buffer may comprise from about 12 mM to about 28 mM of an acetate salt. In some aspects, the buffer may comprise from about 14 mM to about 26 mM of an acetate salt. In some aspects, the buffer may comprise from about 15 mM to about 25 mM of an acetate salt. In some aspects, the buffer may comprise from about 16 mM to about 24 mM of an acetate salt. In some aspects, the buffer may comprise from about 17 mM to about 23 mM of an acetate salt. In some aspects, the buffer may comprise from about 18 mM to about 22 mM of an acetate salt. In some aspects, the buffer may comprise from about 19 mM to about 21 mM of an acetate salt. These ranges include the lower and upper amounts that define the range. In some aspects, the buffer comprises about 20 mM of an acetate salt. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

An acetate buffer can be prepared by acetic acid and sodium acetate trihydrate as exemplified in the table below:

20 mM Sodium Acetate

| pH | Acetic Acid Glacial g/L | Sodium Acetate Trihydrate g/L |
|---|---|---|
| 4.50 | 0.75 | 1.03 |
| 4.70 | 0.61 | 1.34 |
| 5.00 | 0.40 | 1.80 |
| 5.20 | 0.29 | 2.06 |
| 5.50 | 0.16 | 2.35 |
| 6.00 | 0.06 | 2.59 |
| 6.50 | 0.02 | 2.68 |

The buffer may comprise from about 10 mM to about 30 mM of histidine and/or a histidine salt. In some aspects, the buffer may comprise from about 12 mM to about 28 mM of histidine and/or a histidine salt. In some aspects, the buffer may comprise from about 14 mM to about 26 mM of histidine and/or a histidine salt. In some aspects, the buffer may comprise from about 15 mM to about 25 mM of histidine and/or a histidine salt. In some aspects, the buffer may comprise from about 16 mM to about 24 mM of histidine and/or a histidine salt. In some aspects, the buffer may comprise from about 17 mM to about 23 mM of histidine and/or a histidine salt. In some aspects, the buffer may comprise from about 18 mM to about 22 mM of histidine and/or a histidine salt. In some aspects, the buffer may comprise from about 19 mM to about 21 mM of histidine and/or a histidine salt. These ranges include the lower and upper amounts that define the range. In some aspects, the buffer comprises about 20 mM of histidine. Preferably, the histidine is L-histidine. Non-limiting examples of preferred histidine salts include L-histidine monohydrochloride monohydrate, L-histidine citrate, L-histidine glutamate, L-histidine succinate, and L-histidine aspartate. L-histidine monohydrochloride monohydrate is highly preferred.

A histidine buffer can be prepared by mixing histidine base and histidine hydrochloride as indicated in the table below.

20 mM Histidine Hydrochloride

| pH | Histidine base g/L | Histidine HCl g/L |
|---|---|---|
| 4.50 | 0.08 | 4.08 |
| 4.70 | 0.13 | 4.02 |
| 5.00 | 0.25 | 3.86 |
| 5.20 | 0.38 | 3.68 |
| 5.50 | 0.67 | 3.28 |
| 6.00 | 1.47 | 2.21 |
| 6.50 | 2.31 | 1.07 |

A histidine acetate buffer can be prepared by mixing L-histidine base and acetic acid as indicated in the table below.

20 mM Histidine-Acetate

| pH | Volume of 20 mM L-Histidine base (mL) | Volume of 18 mM Acetic Acid (mL) |
|---|---|---|
| 7.50 | 10.00 | 0.00 |
| 5.00 | 10.00 | 14.50 |
| 5.50 | 10.00 | 9.50 |
| 6.00 | 10.00 | 6.00 |
| 6.50 | 10.00 | 3.00 |

The buffer optionally comprises from about 10 mM to about 30 mM of arginine and/or an arginine salt. In some aspects, the buffer may comprise from about 12 mM to about 28 mM of arginine and/or an arginine salt. In some aspects, the buffer may comprise from about 14 mM to about 26 mM of arginine and/or an arginine salt. In some aspects, the buffer may comprise from about 15 mM to about 25 mM of arginine and/or an arginine salt. In some aspects, the buffer may comprise from about 16 mM to about 24 mM of arginine and/or an arginine salt. In some aspects, the buffer may comprise from about 17 mM to about 23 mM of arginine and/or an arginine salt. In some aspects, the buffer may comprise from about 18 mM to about 22 mM of arginine and/or an arginine salt. In some aspects, the buffer may comprise from about 19 mM to about 21 mM of arginine and/or an arginine salt. These ranges include the lower and upper amounts that define the range. In some aspects, the buffer comprises about 20 mM of arginine and/or an arginine salt. Non-limiting examples of preferred arginine salts include arginine acetate, arginine glutamate, arginine succinate, and arginine aspartate. Arginine acetate is highly preferred.

The buffer may comprise from about 100 mM to about 300 mM of sorbitol. In some aspects, the buffer may comprise from about 110 mM to about 290 mM of sorbitol. In some aspects, the buffer may comprise from about 120 mM to about 280 mM of sorbitol. In some aspects, the buffer may comprise from about 150 mM to about 250 mM of sorbitol. In some aspects, the buffer may comprise from about 175 mM to about 225 mM of sorbitol. In some aspects, the buffer may comprise from about 180 mM to about 220 mM of sorbitol. In some aspects, the buffer may comprise from about 185 mM to about 215 mM of sorbitol. In some aspects, the buffer may comprise from about 190 mM to about 215 mM of sorbitol. In some aspects, the buffer may comprise from about 195 mM to about 210 mM of sorbitol. In some aspects, the buffer may comprise from about 197 mM to about 209 mM of sorbitol. In some aspects, the buffer may comprise from about 198 mM to about 208 mM of sorbitol. In some aspects, the buffer may comprise from about 198 mM to about 205 mM of sorbitol. In some aspects, the buffer may comprise from about 199 mM to about 207 mM of sorbitol. In some aspects, the buffer may comprise from about 200 mM to about 210 mM of sorbitol. In some aspects, the buffer may comprise from about 200 mM to about 207 mM of sorbitol. In some aspects, the buffer may comprise from about 200 mM to about 206 mM of sorbitol. In some aspects, the buffer may comprise from about 200 mM to about 205 mM of sorbitol. In some aspects, the buffer may comprise from about 200 mM to about 203 mM of sorbitol. In some aspects, the buffer may comprise from about 201 mM to about 205 mM of sorbitol. In some aspects, the buffer may comprise from about 201 mM to about 204 mM of sorbitol. In some aspects, the buffer may comprise from about 201 mM to about 203 mM of sorbitol. In some aspects, the buffer may comprise from about 202 mM to about 204 mM of sorbitol. In some aspects, the buffer may comprise from about 202 mM to about 203 mM of sorbitol. In some aspects, the buffer may comprise from about 202 mM to about 206 mM of sorbitol. These ranges include the lower and upper amounts that define the range. In some aspects, the buffer comprises about 203 mM of sorbitol.

In preferred embodiments, the buffer is substantially free or free of sodium chloride, citrates, and phosphates.

The antibody formulation preferably comprises a non-ionic surfactant. More preferably, the non-ionic surfactant comprises polysorbate 80. The antibody formulation, including the antibody and the aqueous buffer, preferably comprises from about 0.01% to about 1% (by volume) of polysorbate 80. In some aspects, the antibody formulation comprises from about 0.03% to about 0.7% (by volume) of polysorbate 80. In some aspects, the antibody formulation comprises from about 0.05% to about 0.4% (by volume) of polysorbate 80. In some aspects, the antibody formulation comprises from about 0.075% to about 0.3% (by volume) of polysorbate 80. In some aspects, the antibody formulation comprises from about 0.07% to about 0.25% (by volume) of polysorbate 80. In some aspects, the antibody formulation comprises from about 0.07% to about 0.2% (by volume) of polysorbate 80. In some aspects, the antibody formulation comprises from about 0.07% to about 0.15% (by volume) of polysorbate 80. In some aspects, the antibody formulation comprises from about 0.07% to about 0.14% (by volume) of polysorbate 80. In some aspects, the antibody formulation comprises from about 0.08% to about 0.3% (by volume) of polysorbate 80. In some aspects, the antibody formulation comprises from about 0.08% to about 0.2% (by volume) of polysorbate 80. In some aspects, the antibody formulation comprises from about 0.08% to about 0.15% (by volume) of polysorbate 80. In some aspects, the antibody formulation comprises from about 0.08% to about 0.12% (by volume) of polysorbate 80. In some aspects, the antibody formulation comprises from about 0.08% to about 0.1% (by volume) of polysorbate 80. In some aspects, the antibody formulation comprises from about 0.09% to about 0.15% (by volume) of polysorbate 80. In some aspects, the antibody formulation comprises from about 0.09% to about 0.2% (by volume) of polysorbate 80. In some aspects, the antibody formulation comprises from about 0.09% to about 0.18% (by volume) of polysorbate 80. In some aspects, the antibody formulation comprises from about 0.09% to about 0.11% (by volume) of polysorbate 80. In some aspects, the antibody formulation comprises from about 0.09% to about 0.1% (by volume) of polysorbate 80. These ranges include the lower and upper amounts that define the range. In some aspects, the antibody formulation comprises about 0.1% (by volume) of polysorbate 80.

Polysorbate 20 can also be used in the disclosed compositions instead of polysorbate 80.

The antibody formulation preferably is buffered to an acidic pH. The formulation preferably has a pH of about 4.8 to about 5.6. In some aspects, the formulation has a pH of about 4.9 to about 5.5. In some aspects, the formulation has a pH of about 5.0 to about 5.4. In some preferred aspects, the formulation has a pH of about 5.0 to about 5.3. In some preferred aspects, the formulation has a pH of about 5.0 to about 5.2. In some aspects, the formulation has a pH of about 5.1 to about 5.3. In some aspects, the formulation has a pH of about 5.1 to about 5.5. In some preferred aspects, the formulation has a pH of about 5.1 to about 5.2. In some preferred aspects, the formulation has a pH of about 5.1 to about 5.4. In some aspects, the formulation has a pH of about 5.2 to about 5.4. In some aspects, the formulation has a pH of about 5.2 to about 5.5. In some preferred aspects, the formulation has a pH of about 5.2 to about 5.3. These ranges include the lower and upper amounts that define the range. In some aspects, the formulation has a pH of about 5.2.

In some preferred aspects, the antibody formulation comprises about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 0.7 mM to about 1.3 mM of sodium acetate trihydrate, about 200 mM to about 206 mM of sorbitol, about 10 mM to about 30 mM of L-histidine and/or a histidine salt, 0 mM to about 30 mM of arginine and/or an arginine salt, and about 0.07% to about 0.15% (by volume) of polysorbate 80, and has a pH of about 5.1 to about 5.3. In some aspects, the antibody formulation consists essentially of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 0.7 mM to about 1.3 mM of sodium acetate trihydrate, about 200 mM to about 206 mM of sorbitol, about 12 mM to about 28 mM of L-histidine and/or a histidine salt, 0 mM to about 28 mM of arginine and/or an arginine salt, and about 0.07% to about 0.15% (by volume) of polysorbate 80, and has a pH of about 5.1 to about 5.3. In some aspects, the antibody formulation consists of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 0.7 mM to about 1.3 mM of sodium acetate trihydrate, about 200 mM to about 206 mM of sorbitol, about 14 mM to about 26 mM of L-histidine and/or a histidine salt, 0 mM to about 26 mM of arginine and/or an arginine salt, and about 0.07% to about 0.15% (by volume) of polysorbate 80, and has a pH of about 5.1 to about 5.3. In any such embodiments, the antibody may be present in the formulation at about 37 mg to about 43 mg, or about 38 mg to about 42 mg, or about 39 mg to about 41 mg, or about 40 mg.

In some preferred aspects, the antibody formulation comprises about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 0.8 mM to about 1.2 mM of an acetate salt, about 201 mM to about 205 mM of sorbitol, about 15 mM to about 25 mM of L-histidine and/or a histidine salt, 0 mM to about 25 mM of arginine and/or an arginine salt, and about 0.08% to about 0.15% (by volume) of polysorbate 80, and has a pH of about 5.1 to about 5.3. In some aspects, the antibody formulation consists essentially of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 0.8 mM to about 1.2 mM of an acetate salt, about 201 mM to about 205 mM of sorbitol, about 16 mM to about 24 mM of L-histidine and/or a histidine salt, 0 mM to about 24 mM of arginine and/or an arginine salt, and about 0.08% to about 0.15% (by volume) of polysorbate 80, and has a pH of about 5.1 to about 5.3. In some aspects, the antibody formulation consists of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 0.8 mM to about 1.2 mM of an acetate salt, about 201 mM to about 205 mM of sorbitol, about 17 mM to about 23 mM of L-histidine and/or a histidine salt, 0 mM to about 23 mM of arginine and/or an arginine salt, and about 0.08% to about 0.15% (by volume) of polysorbate 80, and has a pH of about 5.1 to about 5.3. In any such embodiments, the antibody may be present in the formulation at about 37 mg to about 43 mg, or about 38 mg to about 42 mg, or about 39 mg to about 41 mg, or about 40 mg. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

In some preferred aspects, the antibody formulation comprises about 39 mg to about 41 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 0.9 mM to about 1.1 mM of an acetate salt, about 202 mM to about 204 mM of sorbitol, about 18 mM to about 22 mM of L-histidine and/or a histidine salt, 0 mM to about 22 mM of arginine and/or an arginine salt, and about 0.09% to about 0.11% (by volume) of polysorbate 80, and has a pH of about 5.1 to about 5.3. In some aspects, the antibody formulation consists essentially of about 39 mg to about 41 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 0.9 mM to about 1.1 mM of an acetate salt, about 202 mM to about 204 mM of sorbitol, about 19 mM to about 21 mM of L-histidine and/or a histidine salt, 0 mM to about 21 mM of arginine and/or an arginine salt, and about 0.09% to about 0.11% (by volume) of polysorbate 80, and has a pH of about 5.1 to about 5.3. In some aspects, the antibody formulation consists of about 39 mg to about 41 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 0.9 mM to about 1.1 mM of an acetate salt, about 202 mM to about 204 mM of sorbitol, about 20 mM of L-histidine and/or a histidine salt, 0 mM to about 20 mM of arginine and/or an arginine salt, and about 0.09% to about 0.11% (by volume) of polysorbate 80, and has a pH of about 5.1 to about 5.3. In any such embodiments, the antibody may be present in the formulation at about 37 mg to about 43 mg, or about 38 mg to about 42 mg, or about 39 mg to about 41 mg, or about 40 mg. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

In some preferred aspects, the antibody formulation comprises about 40 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 1 mM of an acetate salt, about 203 mM of sorbitol, about 10 mM to about 30 mM of L-histidine and/or a histidine salt, 0 mM to about 30 mM of arginine and/or an arginine salt, and about 0.1% (by volume) of polysorbate 80, and has a pH of about 5.2. In some aspects, the antibody formulation consists essentially of about 40 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 1 mM of an acetate salt, about 203 mM of sorbitol, about 12 mM to about 28 mM of L-histidine and/or a histidine salt, 0 mM to about 28 mM of arginine and/or an arginine salt, and about 0.1% (by volume) of polysorbate 80, and has a pH of about 5.2. In some aspects, the antibody formulation consists of about 40 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 1 mM of an acetate salt, about 203 mM of sorbitol, about 14 mM to about 26 mM of L-histidine and/or a histidine salt, 0 mM to about 26 mM of arginine and/or an arginine salt, and about 26.35 mM of sodium chloride, and about 0.1% (by volume) of polysorbate 80, and has a pH of about 5.2. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

The formulation stabilizes the antibody for improved shelf storage, particularly over a period of months to years. When stored in the formulation, the antibody maintains thermal and colloidal stability during the period of storage. For example, when stored in the formulation, the antibody is stable and exhibits minimal aggregation, flocculation, fragmentation, and denaturation, and the antibody retains it tumor necrosis factor alpha binding activity.

It is preferred that the antibody formulation be stored under refrigerated conditions, and preferably at a temperature of from about 2° C. to about 8° C., including from about 2° C. to about 6° C., and including about 2° C., about 3° C., about 4° C., about 5° C., about 6° C., about 7° C., or about 8° C. The antibody formulation may be stored at such temperatures for at least about 3 months. In some aspects, the antibody formulation may be stored at such temperatures for at least about 6 months. In some aspects, the antibody formulation may be stored at such temperatures for at least about 9 months. In some aspects, the antibody formulation may be stored at such temperatures for at least about 12 months. In some aspects, the antibody formulation may be stored at such temperatures for at least about 15 months. In some aspects, the antibody formulation may be stored at such temperatures for at least about 18 months. During the storage period the antibody is stable and exhibits minimal aggregation, flocculation, fragmentation, and denaturation, and the antibody retains it tumor necrosis factor alpha binding activity such that the antibody formulation may be removed from storage, administered to a patient, and still exhibit therapeutic efficacy against the condition for which the formulation is administered.

The formulation comprises about 10 mg to about 70 mg of antibody. Among this amount of antibody protein is a percentage of antibody monomers in active, native form, as well as a percentage of antibody fragments, antibody aggregates, and denatured or partially denatured antibodies that have reduced or no tumor necrosis binding activity. It is highly preferred that the formulation include a maximal amount of functional antibody monomers and a minimal amount of antibody fragments, aggregates, and structurally altered forms of the antibody with reduced binding activity and/or therapeutic efficacy (relative to the unaltered monomer). For example, the antibody formulation preferably contains at least about 85% by weight of antibody monomers, and less than about 15% by weight of antibody fragments, aggregates, and structurally altered forms with reduced tumor necrosis factor alpha binding activity and/or therapeutic efficacy when stored at about 2° C. to about 8° C. for at least about six months.

In some aspects, the antibody formulation contains at least about 90% by weight of antibody monomers, and less than about 10% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 93% by weight of antibody monomers, and less than about 7% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 95% by weight of antibody monomers, and less than about 5% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 96% by weight of antibody monomers, and less than about 4% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 97% by weight of antibody monomers, and less than about 3% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 98% by weight of antibody monomers, and less than about 2% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 99% by weight of antibody monomers, and less than about 1% by weight of antibody fragments, aggregates, and structurally altered forms with reduced tumor necrosis factor alpha binding activity and/or therapeutic efficacy when stored at about 2° C. to about 8° C. for at least about six months. The amount of antibody monomers and antibody fragments, aggregates, and structurally altered forms may be determined according to any technique suitable in the art, including those described or exemplified herein, including any one or combination of dynamic light scattering (DLS), differential scanning calorimetry (DSC), size exclusion chromatography (SE-UPLC), non-reducing and reducing capillary electrophoresis SDS (NR CE-SDS and R CE-SDS), peptide mapping and particle counting (PC).

In some aspects, the antibody formulation contains at least about 90% by weight of antibody monomers, and less than about 10% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 93% by weight of antibody monomers, and less than about 7% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 95% by weight of antibody monomers, and less than about 5% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 96% by weight of antibody monomers, and less than about 4% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 97% by weight of antibody monomers, and less than about 3% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 98% by weight of antibody monomers, and less than about 2% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 99% by weight of antibody monomers, and less than about 1% by weight of antibody fragments, aggregates, and structurally altered forms with reduced tumor necrosis factor alpha binding activity and/or therapeutic efficacy when stored at about 2° C. to about 8° C. for at least about twelve months. The amount of antibody monomers and antibody fragments, aggregates, and structurally altered forms may be determined according to any technique suitable in the art, including those described or exemplified herein, including any one or combination of dynamic light scattering (DLS), differential scanning calorimetry (DSC), size exclusion chromatography (SE-UPLC), non-reducing and reducing capillary electrophoresis SDS (NR CE-SDS and R CE-SDS), peptide mapping and particle counting (PC).

In some aspects, the antibody formulation contains at least about 90% by weight of antibody monomers, and less than about 10% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 93% by weight of antibody monomers, and less than about 7% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 95% by weight of antibody monomers, and less than about 5% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 96% by weight of antibody monomers, and less than about 4% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 97% by weight of antibody monomers, and less than about 3% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 98% by weight of antibody monomers, and less than about 2% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 99% by weight of antibody monomers, and less than about 1% by weight of antibody fragments, aggregates, and structurally altered forms with reduced tumor necrosis factor alpha binding activity and/or therapeutic efficacy when stored at about 2° C. to about 8° C. for at least about eighteen months. The amount of antibody monomers and antibody fragments, aggregates, and structurally altered forms may be determined according to any technique suitable in the art, including those described or exemplified herein, including any one or combination of dynamic light scattering (DLS), differential scanning calorimetry (DSC), size exclusion chromatography (SE-UPLC), non-reducing and reducing capillary electrophoresis SDS (NR CE-SDS and R CE-SDS), peptide mapping and particle counting (PC).

The disclosure also features methods for treating Rheumatoid Arthritis in a subject in need thereof by administering a therapeutically effective amount of any of the antibody formulations described or exemplified herein. The disclosure also features methods for treating Juvenile Idiopathic Arthritis, Psoriatic Arthritis, Ankylosing Spondylitis, Crohn's Disease, Plaque Psoriasis, Ulcerative Colitis, Inflammatory Bowel Disease, Hidradenitis Suppurativa, or Refractory Asthma by administering a therapeutically effective amount of any of the antibody formulations described or exemplified herein. Therapeutic efficacy is attained, for example, by the ONS-3010 antibody present in the administered formulation. Administration of the antibody formulation may be according to any suitable route, preferably by injection, and more preferably by subcutaneous injection. Administration may be carried out under the direction or supervision of a medical practitioner.

The antibody formulations described and exemplified herein may be for use as a medicament. The antibody formulations described and exemplified herein may be for use in the manufacture of a medicament. The formulations may be for use in the treatment of Rheumatoid Arthritis. The formulations may be for use in the treatment of Juvenile Idiopathic Arthritis. The formulations may be for use in the treatment of Psoriatic Arthritis. The formulations may be for use in the treatment of Ankylosing Spondylitis. The formulations may be for use in the treatment of Crohn's Disease. The formulations may be for use in the treatment of Plaque Psoriasis. The formulations may be for use in the treatment of Ulcerative Colitis. The formulations may be for use in the treatment of Inflammatory Bowel Disease. The formulations may be for use in the treatment of Hidradenitis Suppurativa. The formulations may be for use in the treatment of Refractory Asthma.

The disclosure also features kits. The kits may be used, for example, to practice any of the methods described or exemplified herein. In some aspects, a kit comprises any antibody formulation described or exemplified herein, and instructions for using the antibody formulation in any of the methods or uses described or exemplified herein. The kit may comprise a device for injecting the antibody formulation into a subject, including but not limited to a syringe and needle, or catheter.

The instructions included with the kit may include instructions for administering the antibody formulation in a method for treating Rheumatoid Arthritis, including instructions for injecting the antibody formulation into a Rheumatoid Arthritis patient in need thereof. In some aspects, the instructions included with the kit may include instructions for administering the antibody formulation in a method for treating Juvenile Idiopathic Arthritis, including instructions for injecting the antibody formulation into a Juvenile Idiopathic Arthritis patient in need thereof. In some aspects, the instructions included with the kit may include instructions for administering the antibody formulation in a method for treating Psoriatic Arthritis, including instructions for injecting the antibody formulation into a Psoriatic Arthritis patient in need thereof. In some aspects, the instructions included with the kit may include instructions for administering the antibody formulation in a method for treating Ankylosing Spondylitis, including instructions for injecting the antibody formulation into a Ankylosing Spondylitis patient in need thereof. In some aspects, the instructions included with the kit may include instructions for administering the antibody formulation in a method for treating Crohn's Disease, including instructions for injecting the antibody formulation into a Crohn's Disease patient in need thereof. In some aspects, the instructions included with the kit may include instructions for administering the antibody formulation in a method for treating Plaque Psoriasis, including instructions for injecting the antibody formulation into a Plaque Psoriasis patient in need thereof. In some aspects, the instructions included with the kit may include instructions for administering the antibody formulation in a method for treating Ulcerative Colitis, including instructions for injecting the antibody formulation into a Ulcerative Colitis patient in need thereof. In some aspects, the instructions included with the kit may include instructions for administering the antibody formulation in a method for treating Inflammatory Bowel Disease, including instructions for injecting the antibody formulation into an Inflammatory Bowel Disease patient in need thereof. In some aspects, the instructions included with the kit may include instructions for administering the antibody formulation in a method for treating Hidradenitis Suppurativa, including instructions for injecting the antibody formulation into a Hidradenitis Suppurativa patient in need thereof. In some aspects, the instructions included with the kit may include instructions for administering the antibody formulation in a method for treating Refractory Asthma, including instructions for injecting the antibody formulation into a Refractory Asthma patient in need thereof.

The following examples are provided to describe the disclosure in greater detail. They are intended to illustrate, not to limit, the disclosure.

Example 1

Materials and Methods

Introduction. Antibody ONS-3010 represents a biosimilar of adalimumab, and has been reformulated for enhanced storage stability. It is believed that the modifications to the buffer of the formulation composition may reduce the incidence of injection-site reaction, including injection pain and a burning sensation observed from subcutaneous administration of adalimumab (Kaiser C et al. (2012) Rheumatol. Int. 32:295-9, and Fransson J et al. (1996) J. Pharm. Pharmacol. 48:1012-5). Current adalimumab formulations include (in addition to the antibody), sodium chloride, monobasic sodium phosphate dihydrate, dibasic sodium phosphate dihydrate, sodium citrate, citric acid monohydrate, sorbitol, polysorbate 80, and sterile water for injection. The experimental approach described below included a series of development work to reformulate adalimumab for therapeutic administration. This work focused primarily on evaluating the stressed stability of differing buffer compositions. Four conditions were compared to a control of the adalimumab reference product buffer (per 0.8 ml: 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and Q.S. sterile water for injection, pH 5.2).

Differential Scanning calorimetry. The DSC thermograms was obtained using a MicroCal VP-Capillary DSC system (Malvern Instruments Ltd). Samples were diluted to 0.5 mg/mL using matching formulation buffer as a reference and held for a 15 minute equilibration time at 25° C. The matching formulation buffer blank was subtracted from the samples. The scan rate used for the samples was 60° C./h with a range from 25-95° C. The filtering period used was 8 s and the active cell volume was 1304. The data was analyzed with MicroCal VP-Capillary DSC Automated Analysis Software which utilizes Origin 7.0 software (OriginLab® Corporation, Northampton, Mass.).

Dynamic Light Scattering (DLS). The DLS testing method used a Wyatt DynaPro™ Plate Reader to provide information on protein size distribution and overall colloidal stability in solution. Hydrodynamic radius provided information on the presence of aggregation and confirmation of the molecule's structure in solution. DLS testing provided an orthogonal measure of size distribution in solution under non-denaturing conditions.

Size Exclusion Chromatography (SE-UPLC). SE-UPLC was used to monitor ONS-3010 size variant distribution. The SE-UPLC testing method separates proteins based on size. The method is isocratic with a sodium phosphate running buffer, using a Waters Acquity UPLC BEH200 SEC column (1.7 μm, 4.6×150 mm). Peaks were monitored using absorbance at 280 nm. Species eluting before the monomer peak were aggregates (HMWS) and peaks eluting after the monomer peak were degradants (LMWS).

Non-Reducing and Reducing Capillary Electrophoresis SDS (NR CE-SDS and R CE-SDS). CE-SDS analysis was used to compare ONS-3010 size variants under denaturing conditions, with both non-reducing and reducing conditions, using a Beckman PA800 plus instrument. Capillary gel electrophoresis provides automated analysis of reduced and non-reduced proteins by size to determine protein purity and/or heterogeneity. Samples were treated with either an alkylation or reducing agent and SDS was bound to all proteins via a sample buffer. A polymer matrix was filled into the capillary prior to sample analysis. Samples were electrokinetically introduced to the capillary by an applied voltage, then electrophoresis was performed by applying a constant voltage to the capillary. The SDS treated proteins have mass to charge properties that are proportional to the protein weights, which allows for the separation of the SDS-bound proteins by the differences in molecular weight. Test article proteins were quantified by UV detection at 220 nm.

Cation Exchange Chromatography (CEX). For CEX analysis, a Dionex ProPac WCX-10 (4×250 mm) column was used. Mobile Phase A consisted of 2.4 mM Tris, 1.5 mM Imidazole, 11.6 mM Piperazine, pH 7.0 and mobile Phase B of 9.6 mM Tris, 6.0 mM Imidazole, 11.6 mM Piperazine, pH 11.0. The column temperature was maintained at 30° C. and the chromatogram was monitored and processed at 280 nm wavelength. Protein was eluted when applying a linear gradient from 10% B to 50% B in 23 mins at a flow rate of 0.8 mL/min.

Gradient Info:

| Time | % Mobile Phase A | % Mobile Phase B |
|---|---|---|
| 0 | 90 | 10 |
| 20 | 90 | 10 |
| 25 | 50 | 50 |
| 30 | 50 | 50 |
| 30.5 | 20 | 80 |
| 35 | 20 | 80 |
| 35.5 | 90 | 10 |
| 45 | 90 | 10 |

Modulation of TNF-alpha activity: L929 Cell-Based Bioassay. The primary mechanism of action of adalimumab is the neutralization of circulating TNF-alpha. L929 cell-based bioassay measures cell death/viability. TNF-alpha induces cytotoxicity in L929 cells; relative potency of adalimumab was measured by monitoring live cells through a luminescent tag.

Peptide mapping. N-terminal sequence variants, C-terminal sequence variants, oxidation, deamidation, succinimide formation, isomerization are measured using peptide mapping LC-MS methodologies.

Particle count. The level of aggregates and particulates is a critical quality attribute to assess for liquid protein formulations. The presence of aggregates and particulates may negatively impact product quality.

Example 2

Results

This experimental series of studies focused on buffer composition, strength, and ability to achieve the desired pH of 5.2. Buffers tested included citrate and phosphate (which are used in the reference product formulation) and histidine acetate. Sodium chloride and mannitol concentrations (equivalent to those in adalimumab reference formulation) were added to conditions throughout experimental series 1 experiments. The following conditions/formulations were evaluated for stability of the adalimumab active.

1. Adalimumab Citrate-Phosphate Formulation (Commercial Humira® Formulation)
    105.45 mM Sodium Chloride
    5.53 mM Sodium Phosphate, Monobasic Dihydrate
    8.57 mM Sodium Phosphate, Dibasic Dihydrate
    1.02 mM Sodium Citrate, Dihydrate
    6.19 mM Citric Acid, Monohydrate
    65.87 mM Mannitol
    0.1% Polysorbate-80
    pH 5.2

2. Adalimumab Acetate Salt Formulation
    26.35 mM Sodium Chloride
    20 mM Acetate
    203.00 mM Mannitol
    0.1% Polysorbate-80
    pH 5.2

3. Adalimumab Histidine Formulation
   4.1% Sorbitol
   5 mM L-histidine and L-histidine monohydrochloride monohydrate
   0.015% Polysorbate 80
   pH 5.5
4. Adalimumab Acetate Formulation
   17 mM acetate
   4.7% sorbitol
   0.01% polysorbate 20
   pH 5.2
5. Adalimumab Histidine Acetate Formulation
   20 mM Histidine Acetate
   4% Mannitol (or 4% Sorbitol)
   0.1% Polysorbate 80
   pH 5.2

From this series of experiments, it was observed that some buffers were better than others at achieving and maintaining stability of the adalimumab active. The following is a summary of the results with reference to the FIGS.

Referring to FIGS. 1-4, SE-UPLC was used to measure and predict the long term colloidal stability of the adalimumab formulations of certain of the conditions 1-4 by looking at the colloidal behavior at various temperature ranges. As shown in FIG. 1, 10 days at an elevated temperature of 55° C. causes significant aggregation (increasing SE-UPLC high molecular weight species or HMWS is observed for condition 1 (Humira®) with a substantially lesser amount of aggregation for the conditions 3 and 4, respectively. Both conditions 3 and 4 were free of added NaCl. Such formulations lacking NaCl exhibited improved stability toward aggregation.

Figure 2:
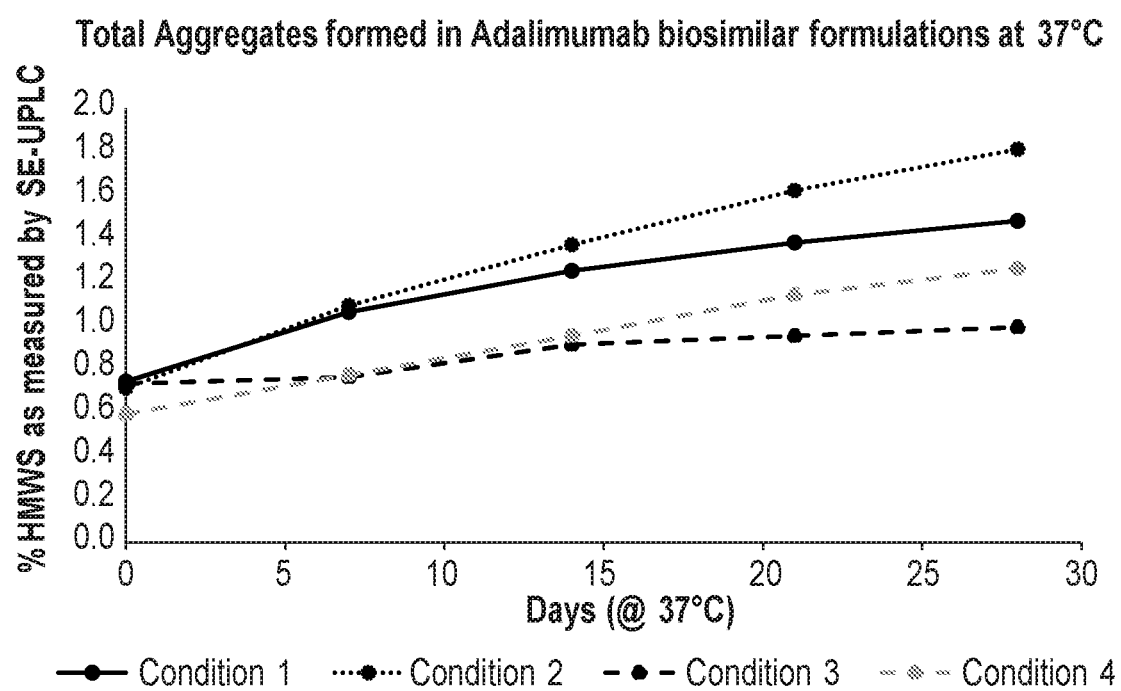
FIG. 2 is an SE-UPLC % high molecular weight species (HMWS) micrograph showing trends in aggregation in adalimumab formulations at 37° C. for 28 days.
Figure 3:
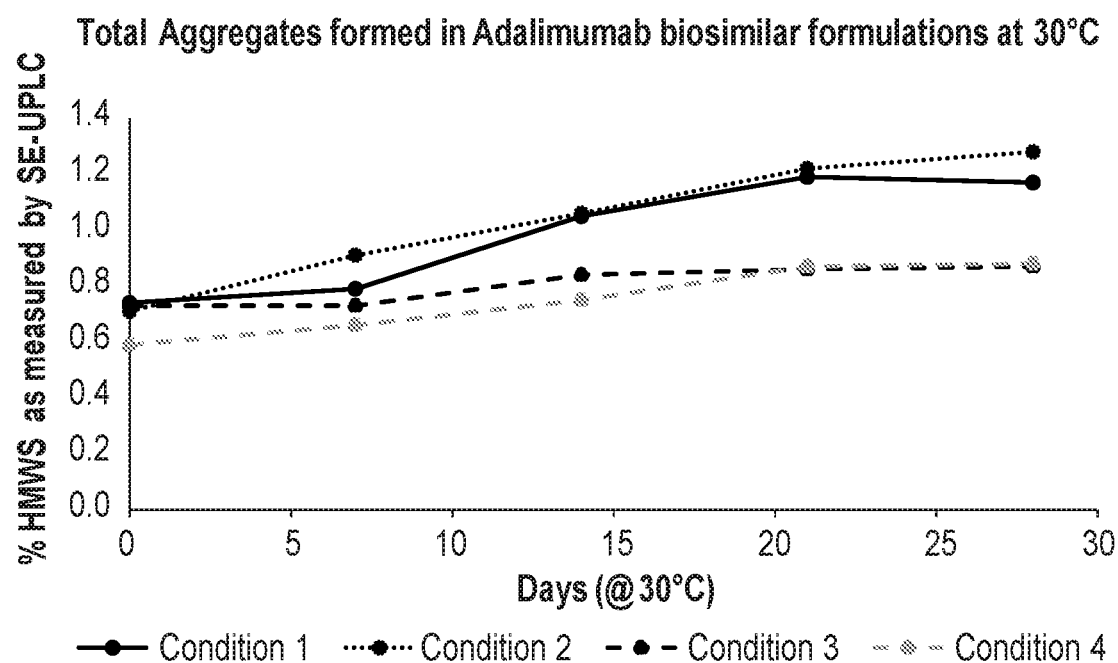
FIG. 3 is an SE-UPLC % high molecular weight species (HMWS) micrograph showing trends in aggregation in adalimumab formulations at 30° C. for 28 days.
Figure 4:
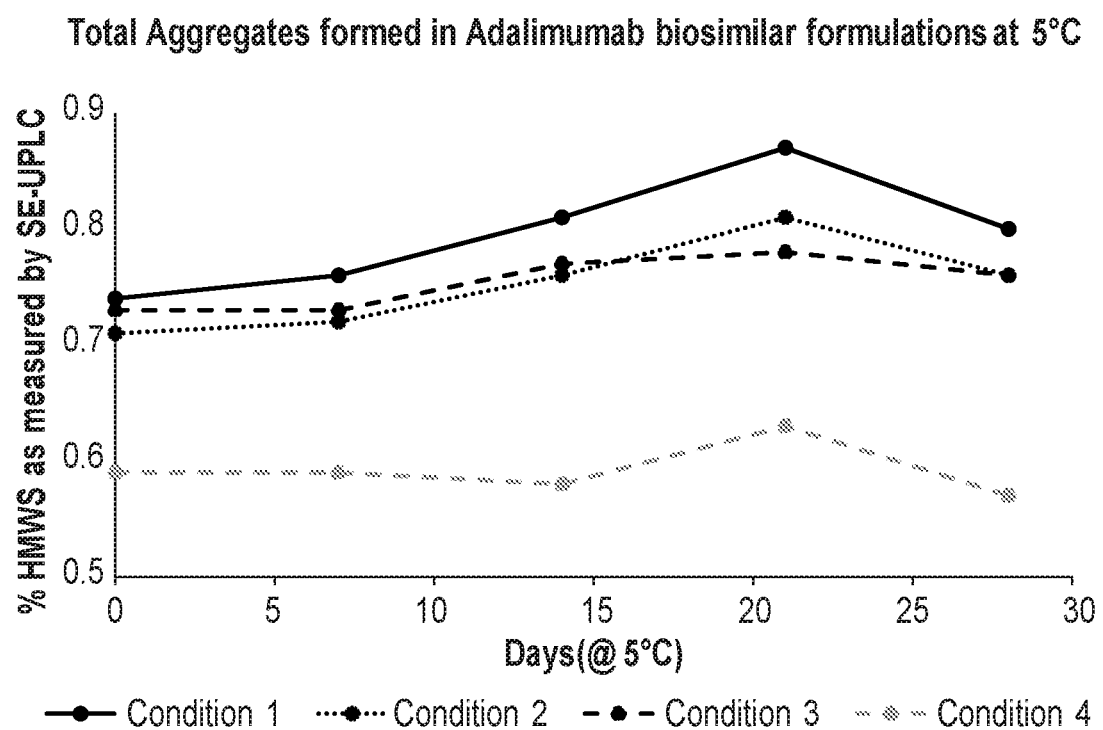
FIG. 4 is an SE-UPLC % high molecular weight species (HMWS) micrograph showing trends in aggregation in adalimumab formulations at 5° C. for 28 days.

FIGS. 2-4 illustrate the aggregation observed over a 28 day period (real time) for conditions 1-4. As the temperature is lowered, the overall percentage of agglomeration of adalimumab (% HMWS as measured by SE-UPLC) decreases. It is evident that conditions 3 and 4 are more stable through a range of temperatures including 37° C., 30° C., and 5° C. for a period of 28 days in solution.

Freeze-thaw cycling was conducted for samples in the candidate formulations at two temperatures: −20° C. and −80° C. Samples were placed in freezers set to the appropriate temperature and allowed to freeze thoroughly (for at least one hour). Samples were then removed from the freezer and allowed to thaw at 25° C. (approximately 1 hour). This freezing step plus the thawing step constituted a single cycle. Samples were subjected to up to 3 freeze-thaw cycles, and then analyzed together by SE-UPLC, with a subset of samples also tested by NR CE-SDS.

Figure 5:
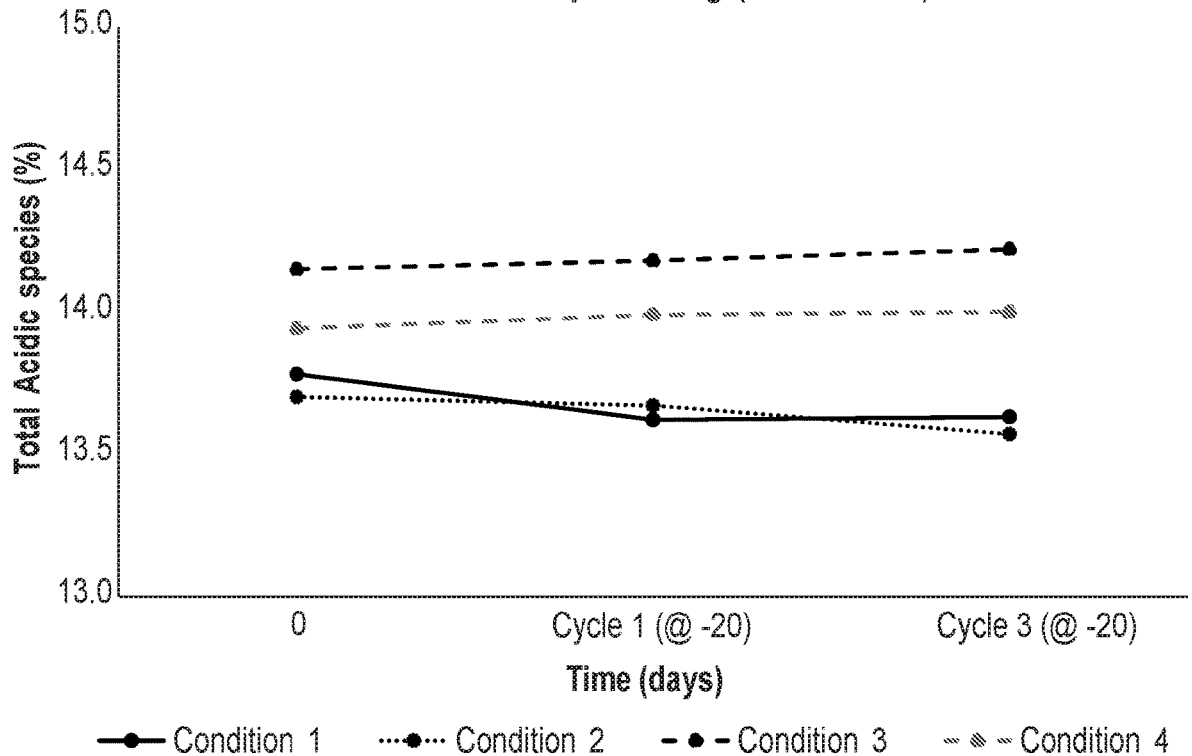
FIG. 5 is a cation exchange chromatography (CEX-HPLC) chromatogram showing the % total acid species of samples of conditions 1-4 after exposure to three freeze/thaw cycles at −20° C.
Figure 6:
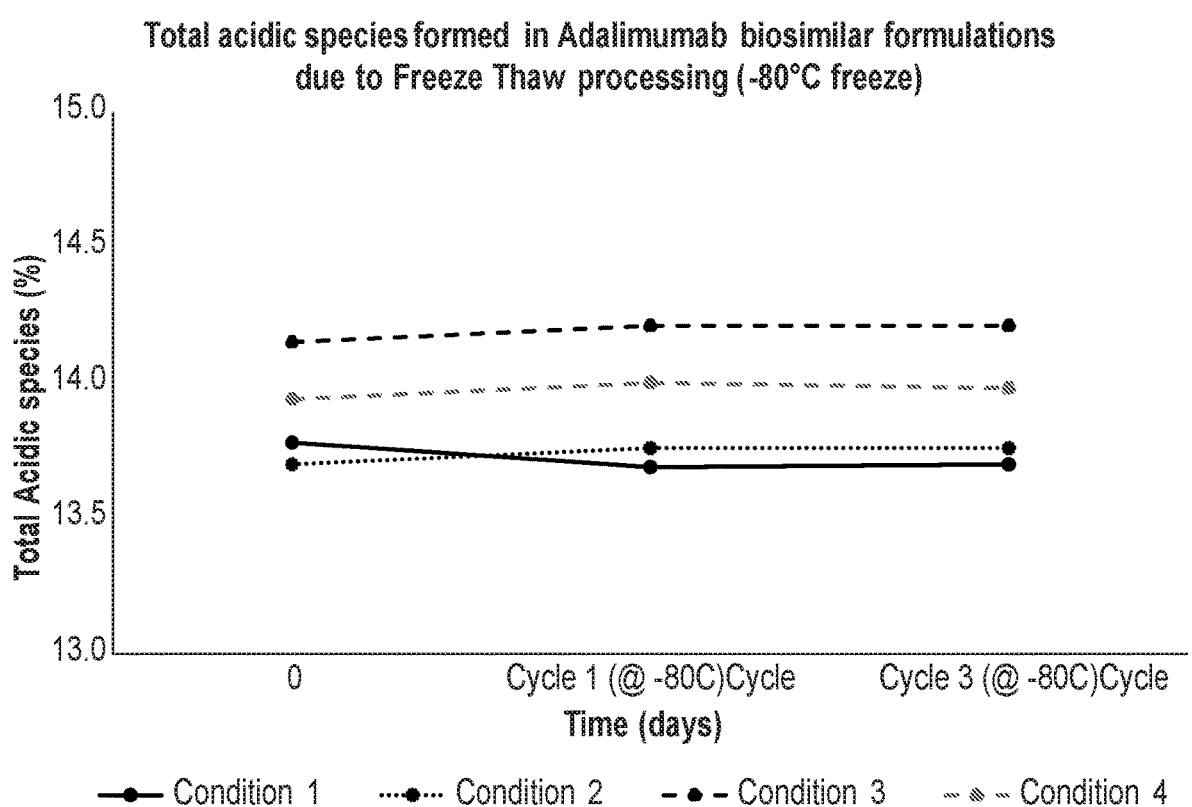
FIG. 6 is a cation exchange chromatography (CEX-HPLC) chromatogram showing the % total acid species of samples of conditions 1-4 after exposure to three freeze/thaw cycles at −80° C.

FIGS. 5-6 illustrate the results of cation exchange chromatography (CEX-HPLC) of samples of conditions 1-4 after exposure to three freeze/thaw cycles at −20° C. (FIG. 5) and −80° C. (FIG. 6). This test provides a broad view of many physicochemical changes that can manifest themselves as changes in molecular charge. This includes specific charge based modifications such as deamidation, isomerization, and pyroglutamine formation. CEX-HPLC profiles were monitored for time zero through 3 freeze-thaw cycles, and the results were illustrated in FIGS. 5 and 6.

Figure 7:
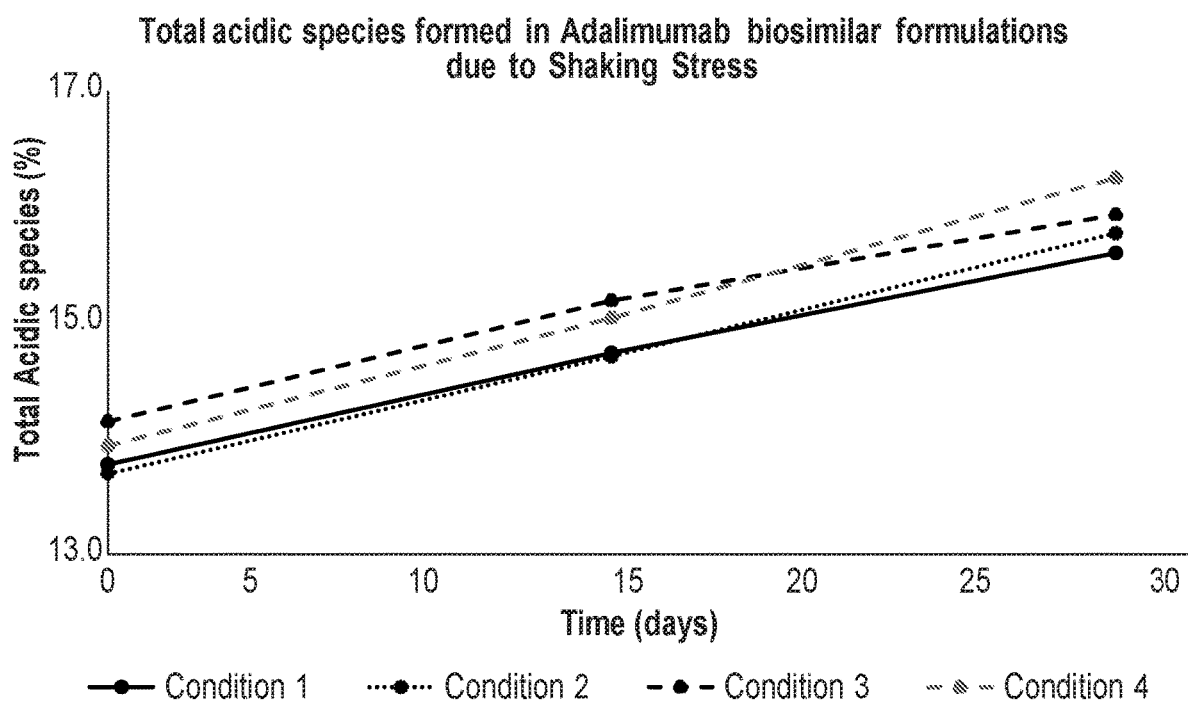
FIG. 7 is a cation exchange chromatography (CEX-HPLC) chromatogram showing the % total acid species of samples of conditions 1-4 after exposure shaking stress.

In order to assess the protective ability of the formulation toward shear forces, a shaking study was conducted in glass vials (1 mL fills) placed in an orbital shaking incubator set to 150 rpm at 25° C. FIG. 7 illustrates the results of cation exchange chromatography (CEX-HPLC) of samples of conditions 1-4 after continuous shaking stress at 25° C. This test provides a broad view of many physicochemical changes that can manifest themselves as changes in molecular charge. This includes specific charge based modifications such as deamidation, isomerization, and pyroglutamine formation. CEX-HPLC profiles were monitored for time zero through day 28.

To probe the behavior of the test formulations toward a stressed condition of elevated temperature, samples were incubated at 55° C. for up to 10 days, and then tested by multiple analytical methods. While 55° C. is well above storage conditions and any expected short-term handling conditions that would be encountered in the clinic, the stressed stability arm is extremely useful at highlighting formulation ability to protect from a myriad of forced degradation events that dominate at higher temperature.

Figure 8:
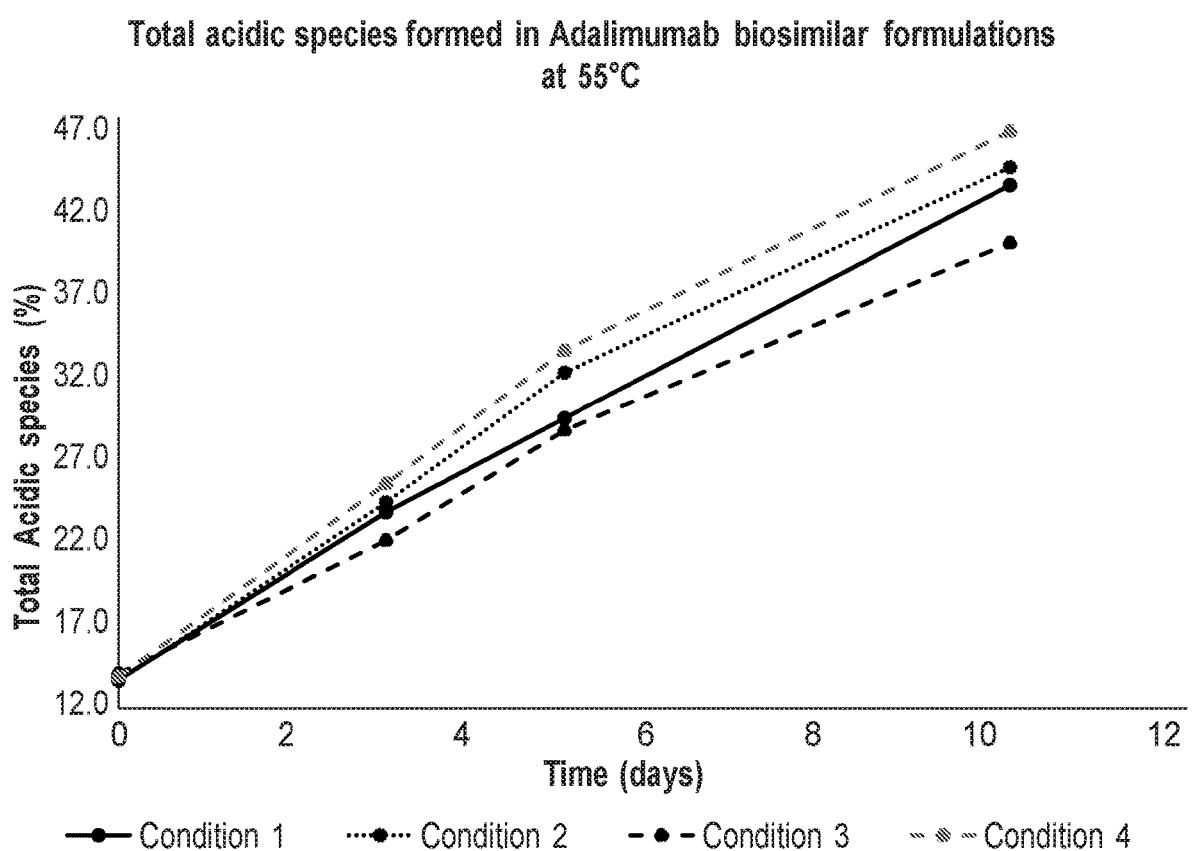
FIG. 8 is a plot of total acidic species formed in adalimumab biosimilar formulations at 55° C. over a 10 day period.

FIG. 8 illustrates the results of cation exchange chromatography (CEX-HPLC) of samples of conditions 1-4 treated at 55° C. This test provides a broad view of many physicochemical changes that can manifest themselves as changes in molecular charge. This includes specific charge based modifications such as deamidation, isomerization, and pyroglutamine formation, but can also reveal more subtle conformational shifts that can begin to occur at elevated temperatures. CEX-HPLC profiles were monitored for time zero through day 10.

Figure 9:
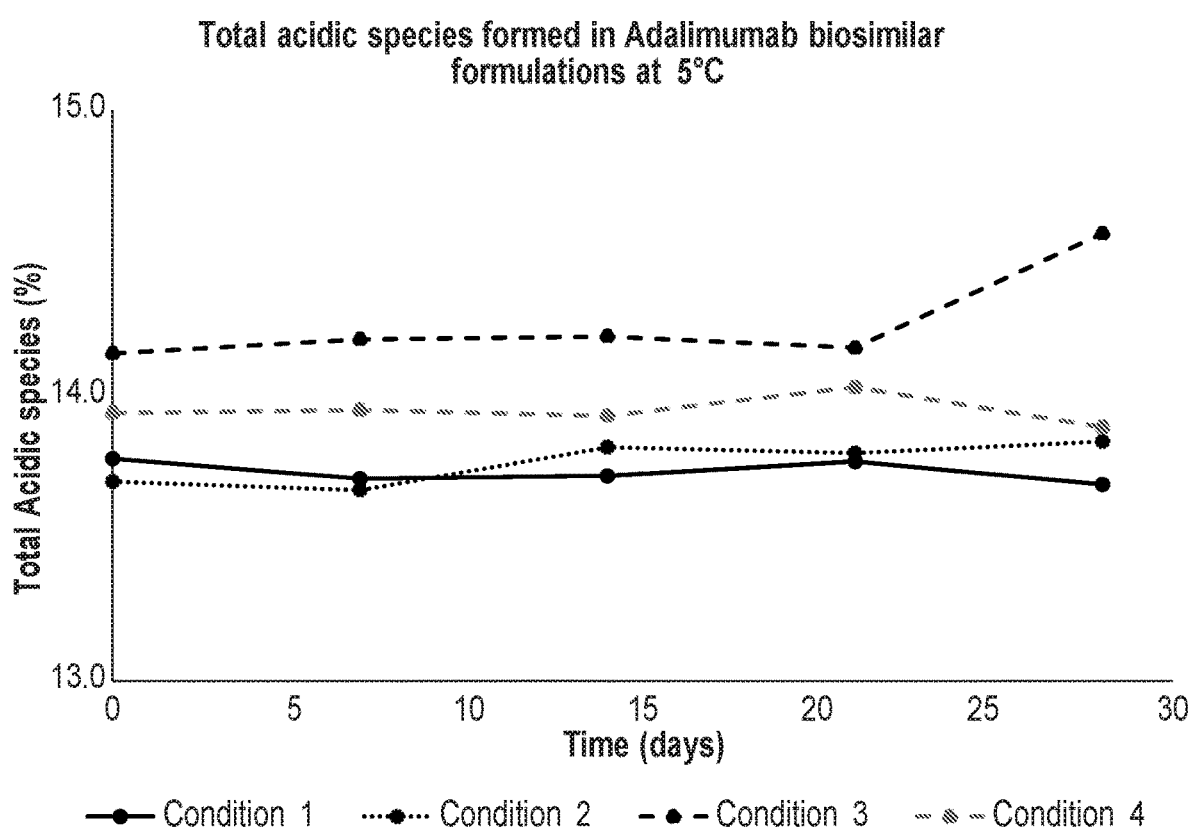
FIG. 9 is a plot of total acidic species formed in adalimumab biosimilar formulations at 5° C. over a 28 day period.
Figure 10:
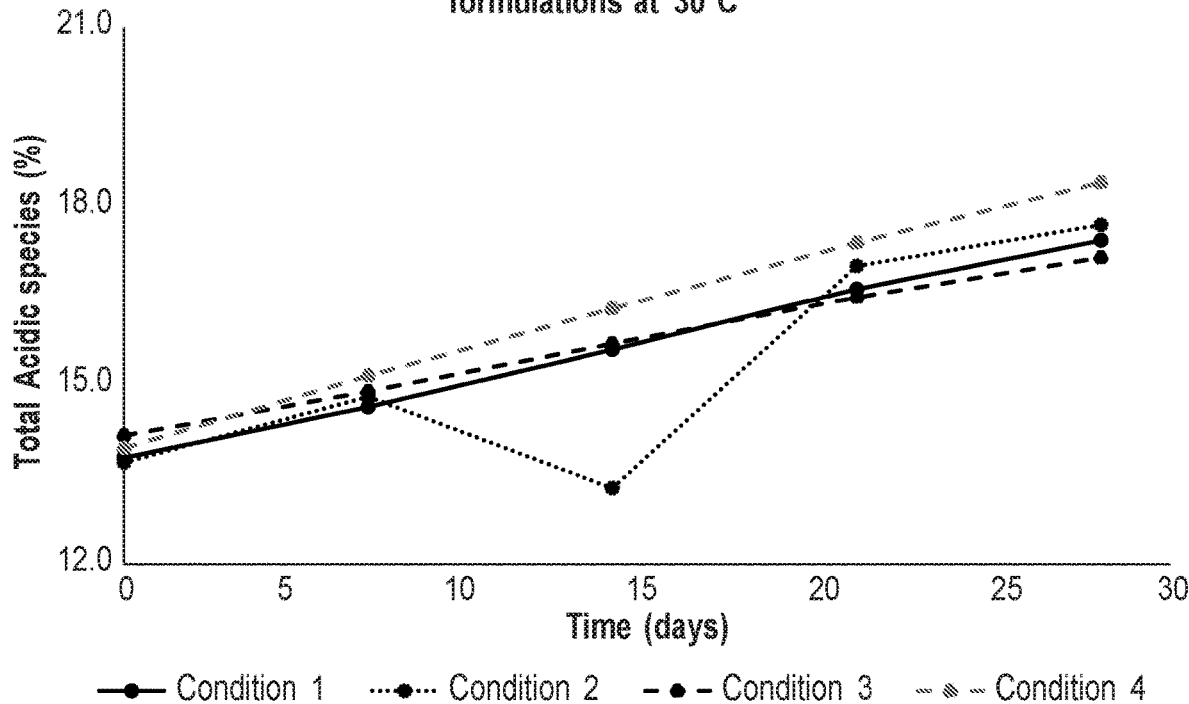
FIG. 10 is a plot of total acidic species formed in adalimumab biosimilar formulations at 30° C. over a 28 day period.
Figure 11:
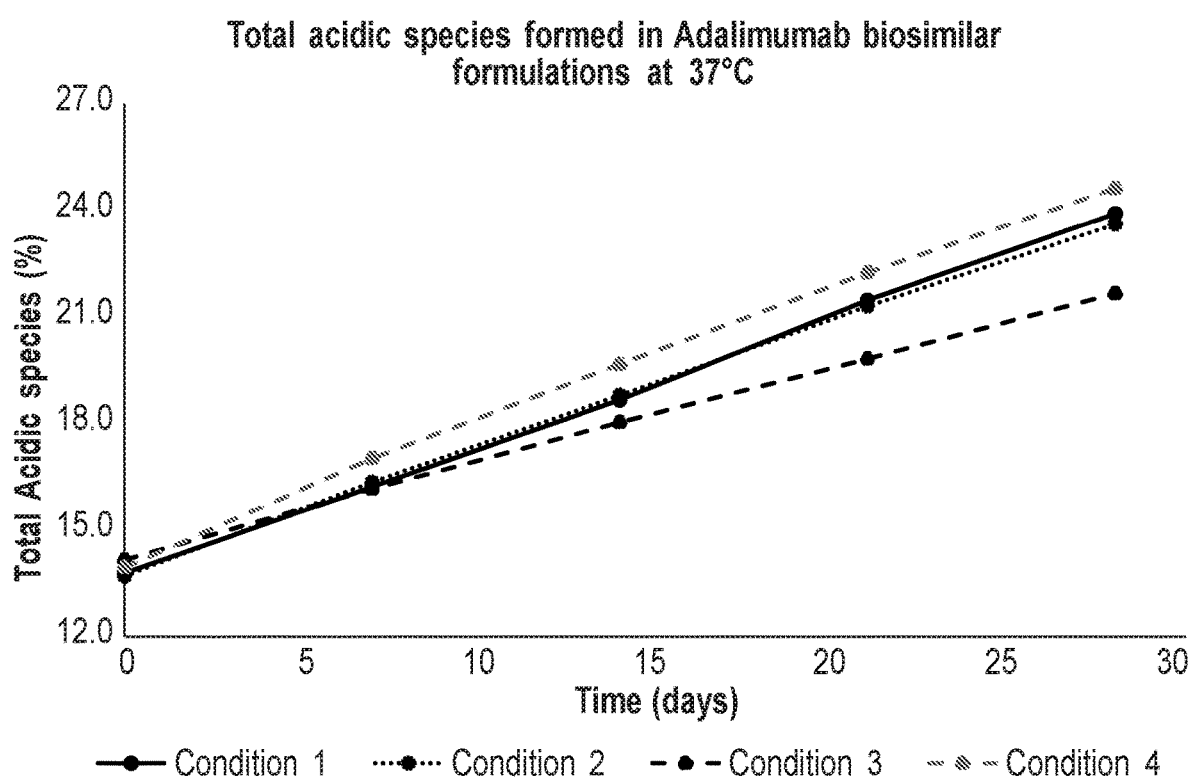
FIG. 11 is a plot of total acidic species formed in adalimumab biosimilar formulations at 37° C. over a 28 day period.

FIGS. 9-11 illustrates the results of cation exchange chromatography (CEX-HPLC) of samples of conditions 1-4 treated at 5° C., 30° C., and 37° C., respectively, in terms of acidic specie formation. This test provides a broad view of many physicochemical changes that can manifest themselves as changes in molecular charge. This includes specific charge based modifications such as deamidation, isomerization, and pyroglutamine formation, but can also reveal more subtle conformational shifts that can begin to occur at elevated temperatures. CEX-HPLC profiles were monitored for time zero through day 28. Here again, the compositions are all most stable at lower temperatures and more acidic species develop over time at higher temperatures. At such higher temperatures, there does not seem to be much difference when comparing the 4 conditions tested.

Figure 12:
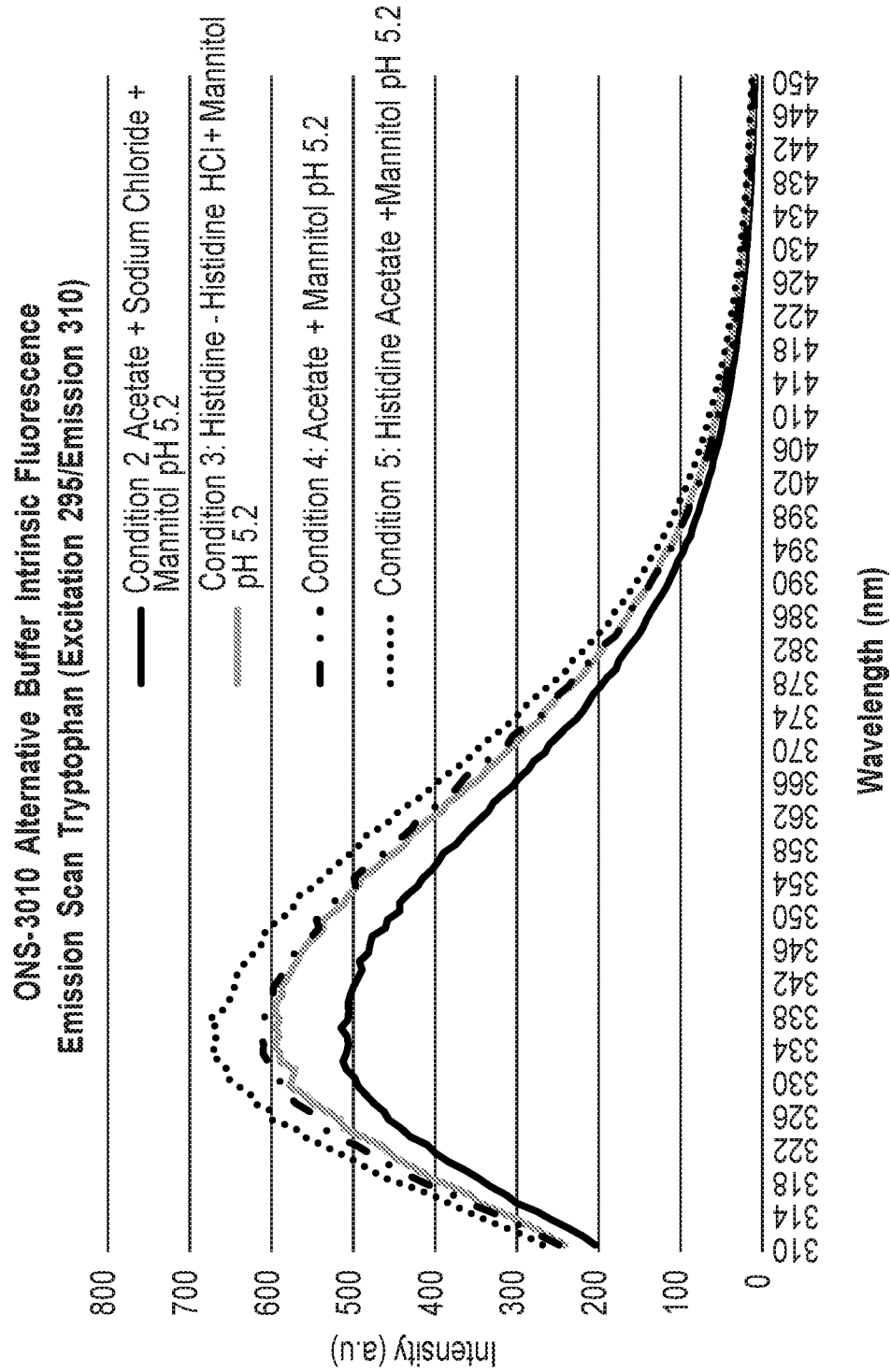
FIG. 12 is a spectrograph showing the intrinsic fluorescence emission scan tryptophan (Excitation 295/Emission 310) for adalimumab biosimilar formulations with alternative buffers.

FIG. 12 is an emission scan showing intrinsic fluorescence emission of the formulations of conditions 2-5. While the fluorescence intensity varies for all the compositions, the wavelength maximum is similar indicating identical overall microenvironment for all tryptophan and tyrosine residues in the antibody.

Figure 13:
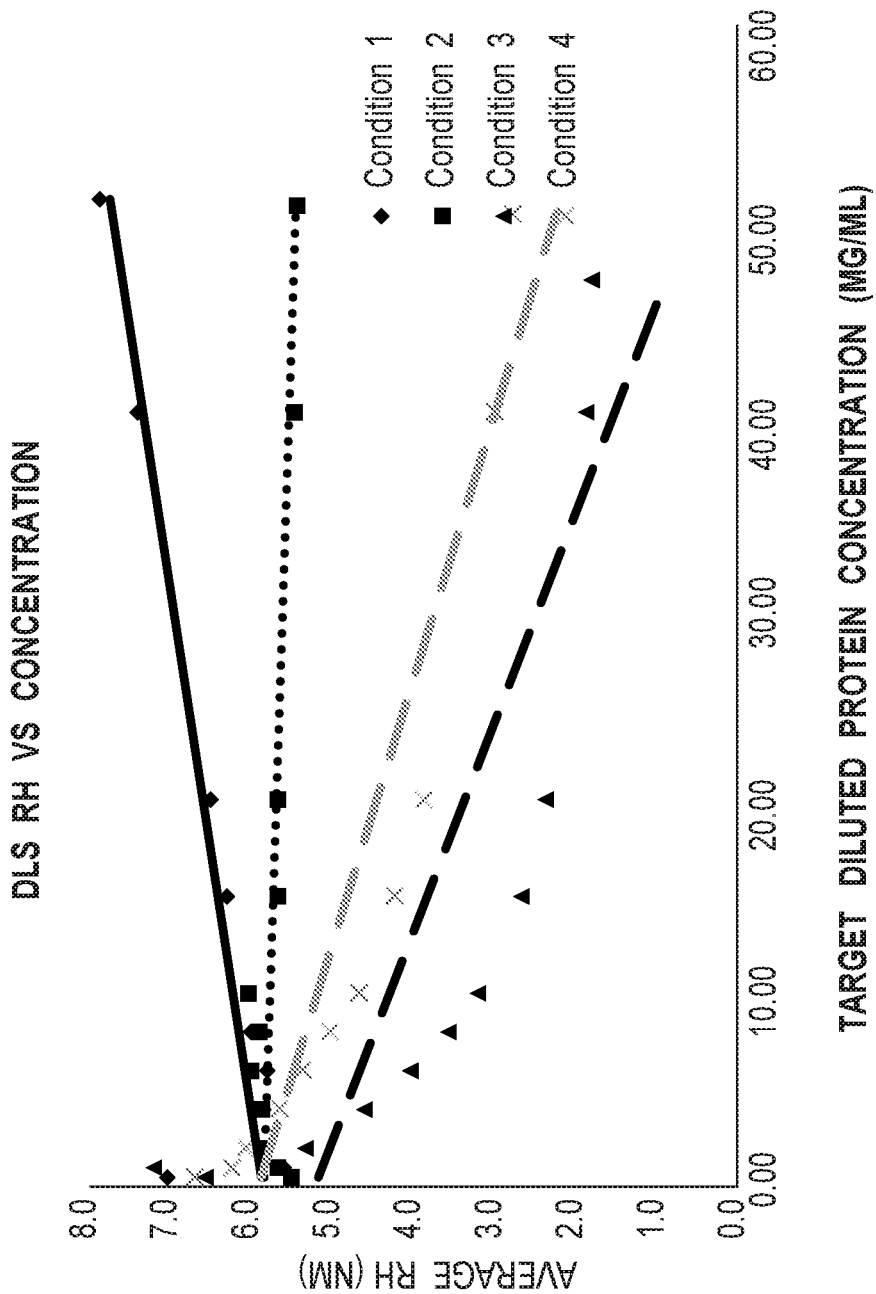
FIG. 13 is a plot of DLS RH versus concentration of diluted protein for evaluated buffer systems.

Referring to FIG. 13, dynamic light scattering (DLS) was used to monitor the hydrodynamic radius Rh (size) of protein molecules in solution versus the concentration of diluted protein in solution. Hydrodynamic radius size in the 5-6 nanometer range under lower (~1 mg/mL) protein concentration are typical for monomeric monoclonal antibodies (about 140 kDa in size); this size increases with protein concentration for condition 1, possibly due to crowding, self-association, or aggregation. Such higher sizes should typically be avoided under formulation conditions since they are indicative of an inherently unstable condition. Conditions 3 and 4, however, show significantly less agglomeration as the protein concentration increases.

Figure 14:
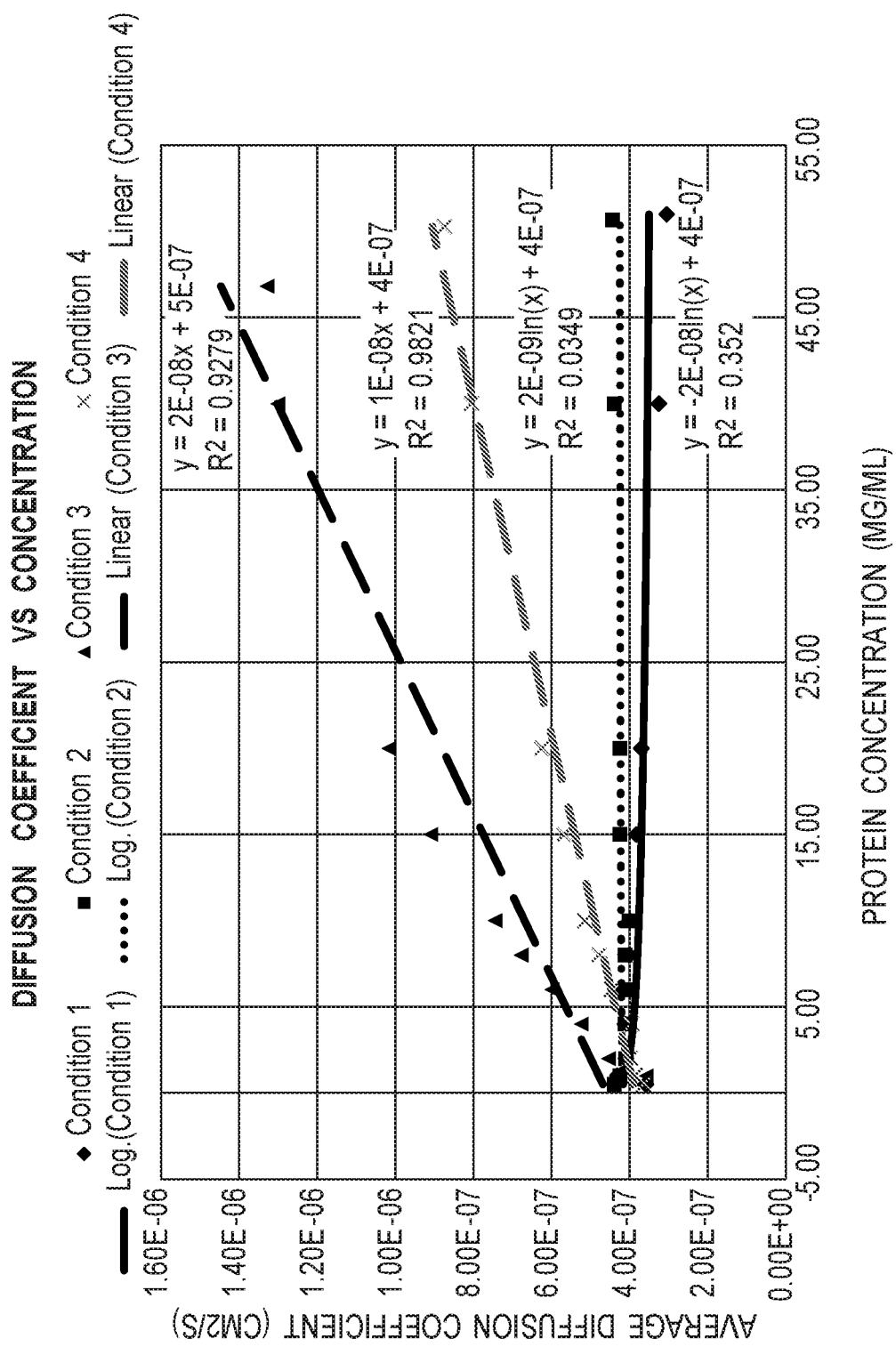
FIG. 14 is a plot of diffusion coefficient versus protein concentration for evaluated buffer systems.

FIG. 14 correlates well to that illustrated in FIG. 13 in that the agglomeration promoting conditions (e.g., Condition 1) have poor diffusivity compared to the conditions having smaller particles as the protein concentration increases.

Results based on stressed and accelerated stability studies indicate promising reformulation conditions with comparable and/or improved degradation rates relative to that of the antibody in the adalimumab reference formulation.

Figure 15:
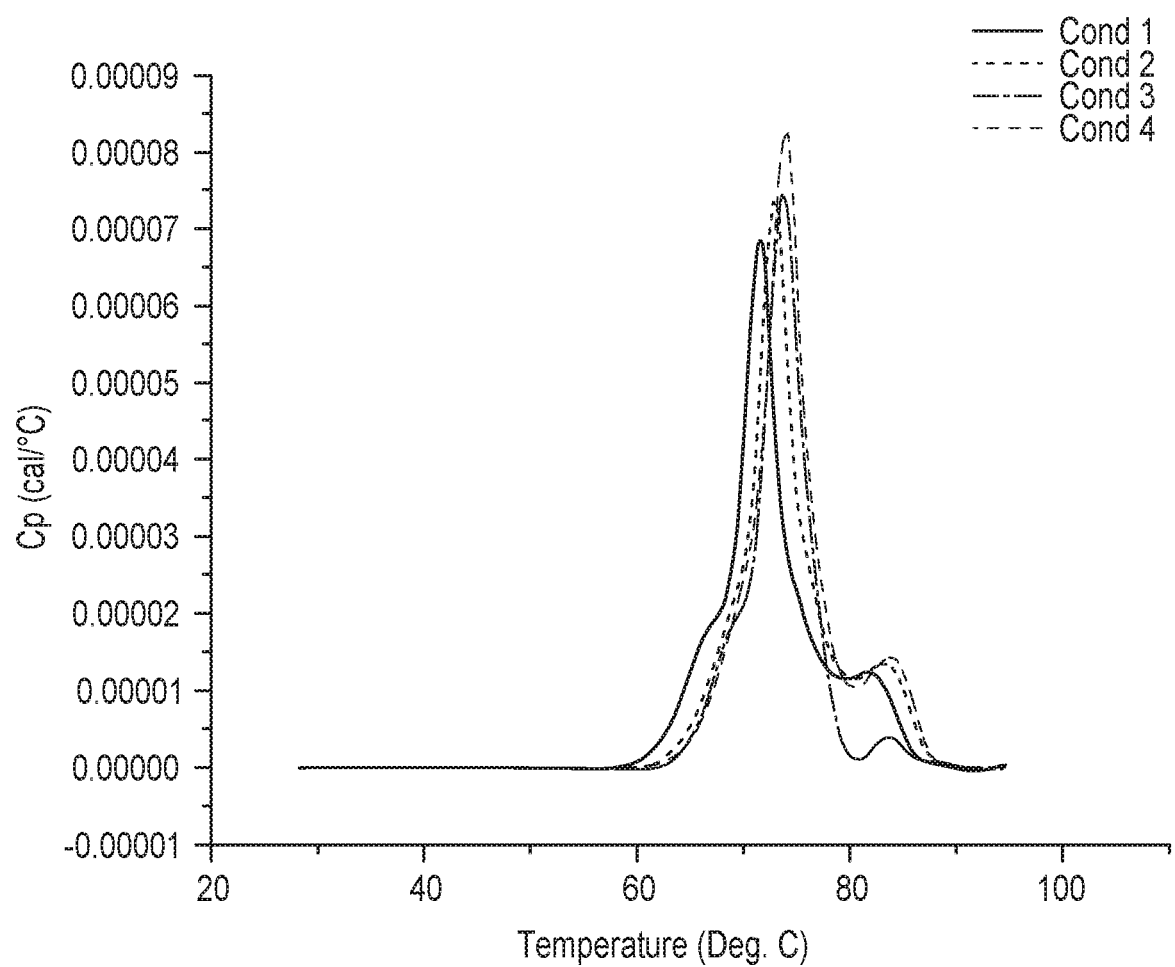
FIG. 15 is a Differential Scanning calorimetry (DSC) plot depicting the thermal stability and related unfolding (thermograms) for all formulation compositions.

FIG. 15 shows the thermal stability and related unfolding (thermograms) for all formulation compositions as measured by Differential Scanning calorimetry (DSC). The $T_{onset}$ and $T_m$ for the protein under all conditions besides Condition 1 is higher than that for Condition 1.

The invention is not limited to the embodiments described and exemplified above, but is capable of variation and modification within the scope of the appended claims.

Example 3

Results

This experimental series of studies focused on buffer composition, strength, and evaluation of the ability of histidine-acetate buffer pH of 5.2 to achieve conformational and colloidal stabilization of Adalimumab.

Figure 16:
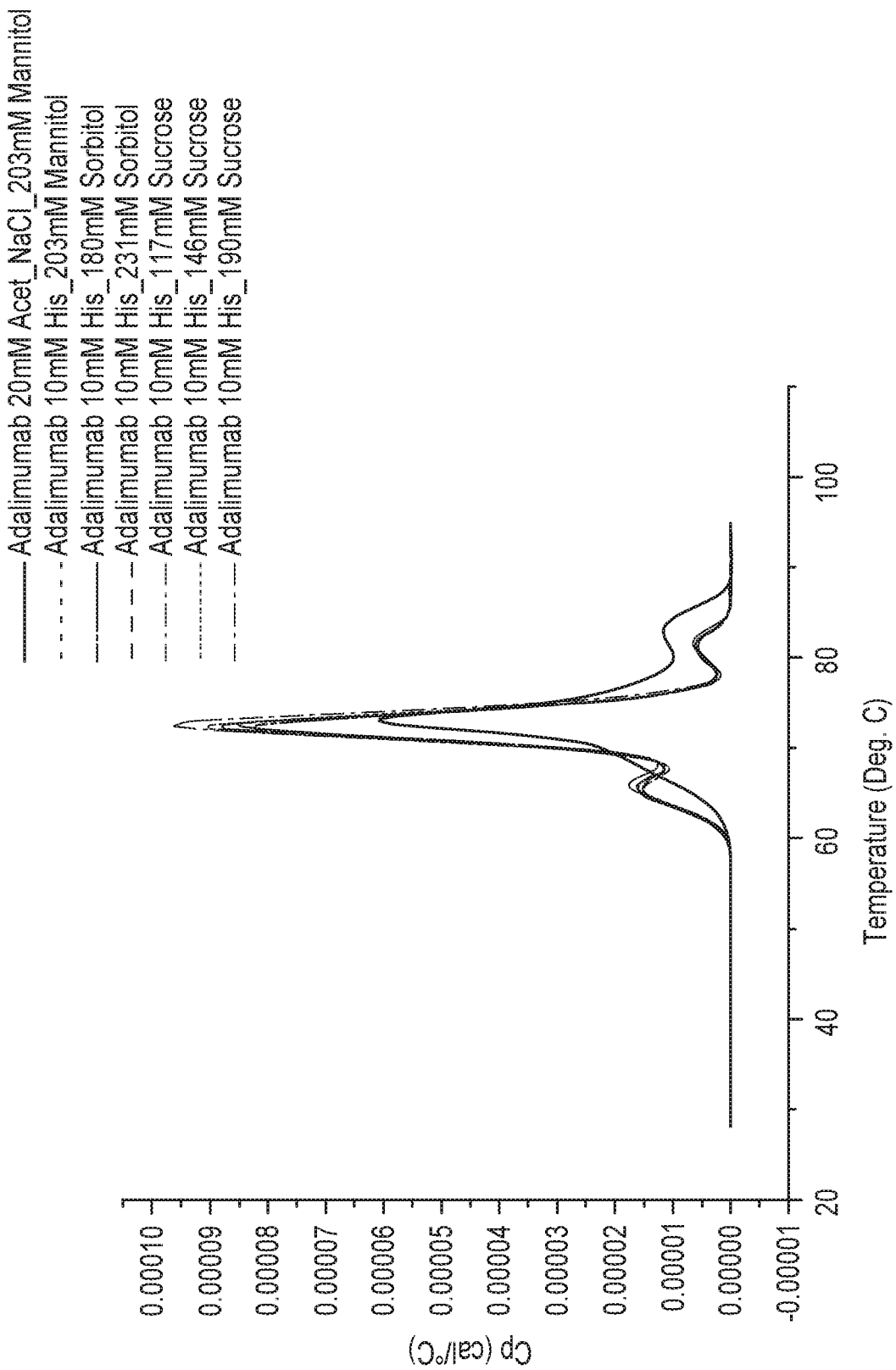
FIG. 16 is a DSC plot depicting a thermal stability profile of Adalimumab in 10 mM histidine buffer pH 5.2. Each composition employs a different type and concentration of sugar for stabilization.

Conformational and Colloidal Stability of Adalimumab in Histidine Buffer:

Conformational stability of Adalimumab in Histidine buffer pH 5.2 is evaluated by DSC. 3 types of sugars (mannitol, sorbitol, sucrose) are used as stabilizers along with Histidine buffer pH 5.2. The findings of the conformational stability trends are summarized in FIG. 16. At lower pH of 5.2, an early unfolding event is observed which in case of IgG1 antibody is the $C_H2$ domain. Data from conformational study suggest that Adalimumab should be formulated in Histidine buffer at a pH>5.2.

Figure 17:
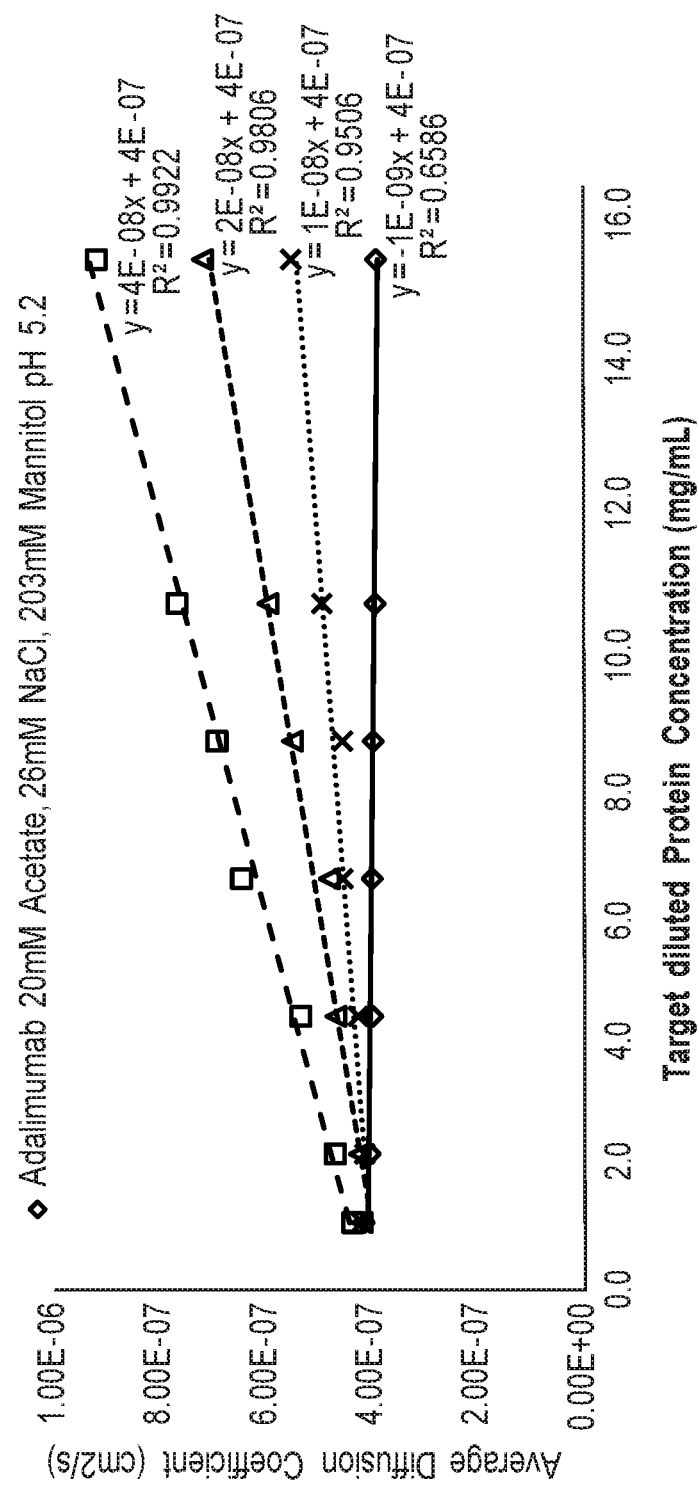
FIG. 17 is a graph depicting the effect of histidine buffer molarity on the colloidal stability of Adalimumab. Histidine buffer at pH 5.2 including mannitol as a stabilizer.
Figure 18:
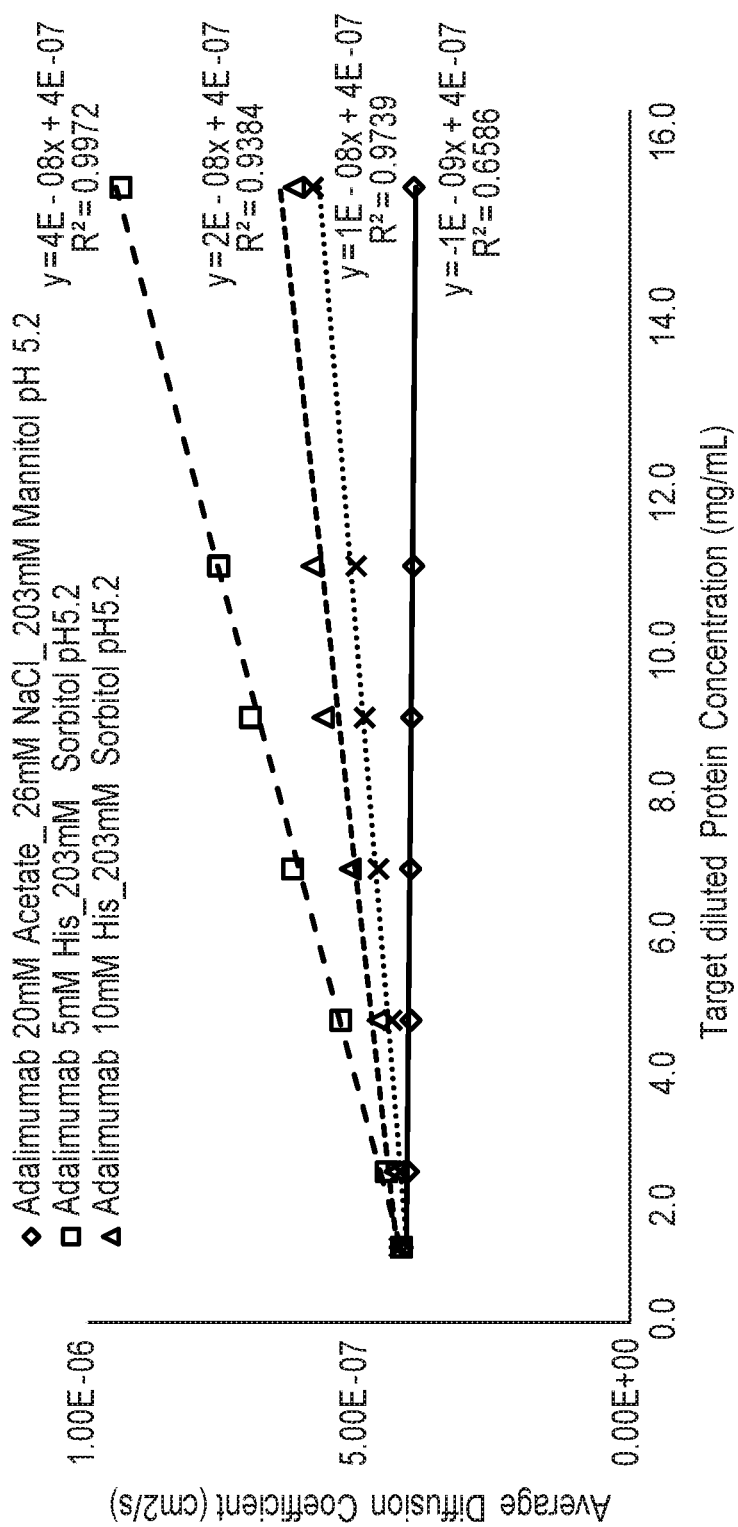
FIG. 18 is a graph depicting the effect of histidine buffer molarity on the colloidal stability of Adalimumab. Histidine buffer at pH 5.2 including sorbitol as a stabilizer.
Figure 19:
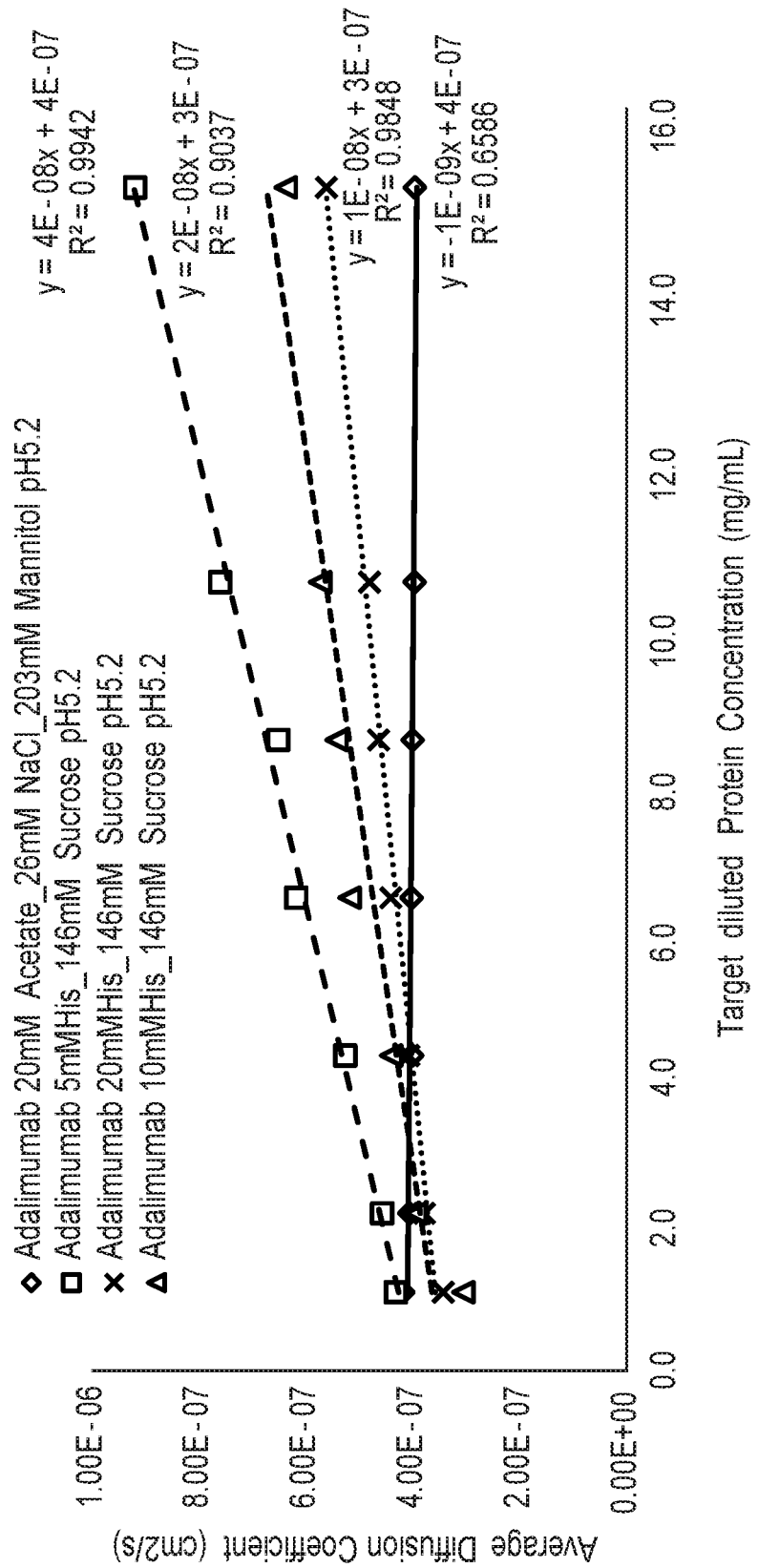
FIG. 19 is a graph depicting the effect of histidine buffer molarity on the colloidal stability of Adalimumab. Histidine buffer at pH 5.2 including sucrose as a stabilizer.

Colloidal stability of Adalimumab in Histidine buffer pH 5.2 is evaluated at varying molar concentrations of the buffer. 3 types of sugars (mannitol, sorbitol, sucrose) are used as stabilizers with these buffers. The findings of the colloidal stability trends are summarized in FIGS. 17, 18 and 19.

The colloidal stability for Adalimumab as depicted by an increase in average diffusion coefficient increases with decreasing buffer molarity. This trend is similar for the three types of sugars evaluated. Hence for better long term stability, lower molarity buffers would be considered ideal.

Figure 20:
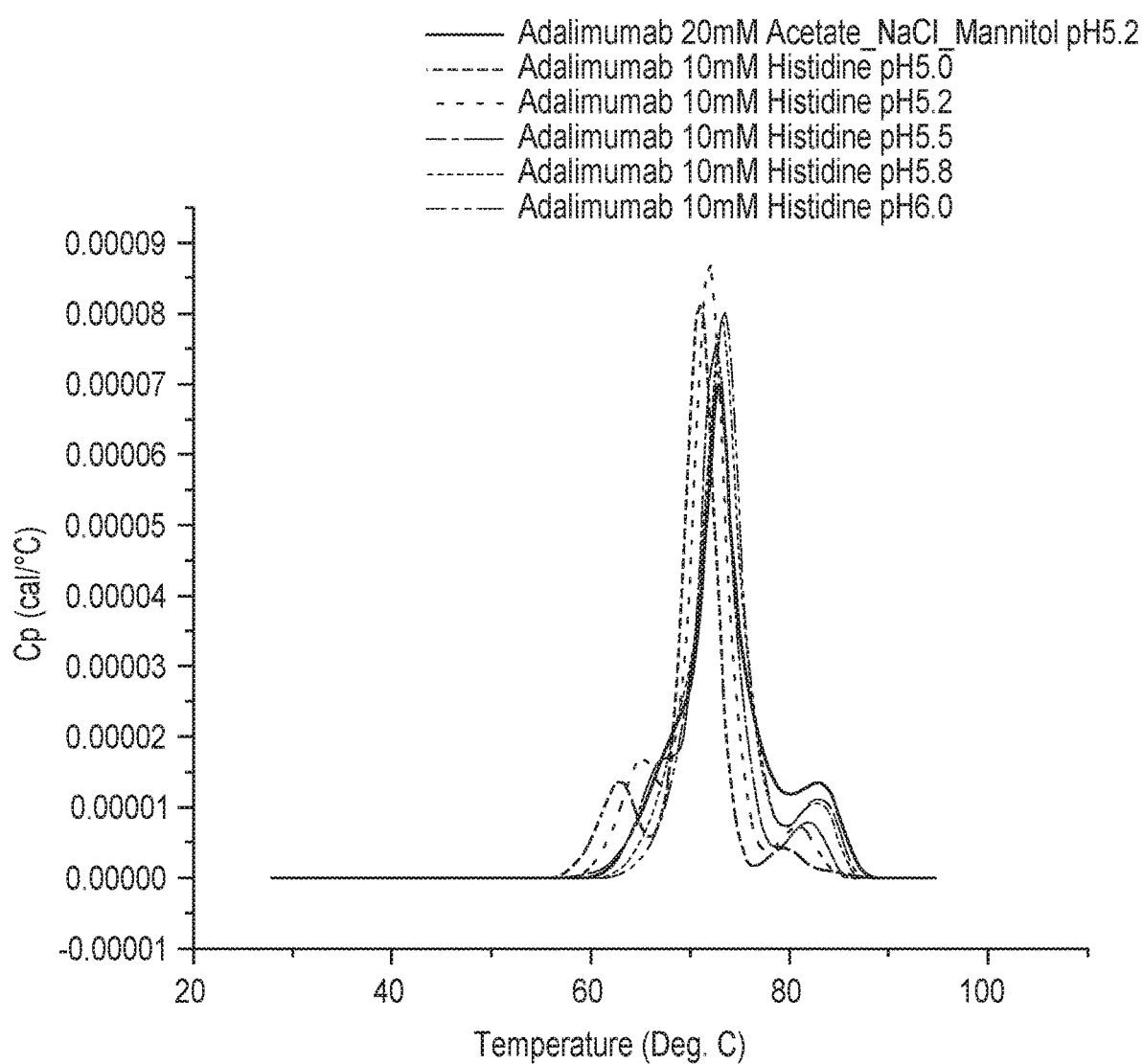
FIG. 20 is a DSC plot depicting a thermal stability profile of Adalimumab in 10 mM histidine buffer having a pH ranging between 5.0 and 6.0.

Effect of pH on Conformational and Colloidal Stabilization of Adalimumab in Histidine Buffer:

Conformational stability of Adalimumab in Histidine buffer is evaluated at varying pH in the range of pH 5 to 6. The findings of the conformational stability trends are summarized in FIG. 20. At lower pH (<5.5), an early unfolding event is observed which in case of IgG1 antibody is the $C_H2$ domain. Data from conformational study suggest that Adalimumab should be formulated at a pH of 6.0 in Histidine buffer.

Figure 21:
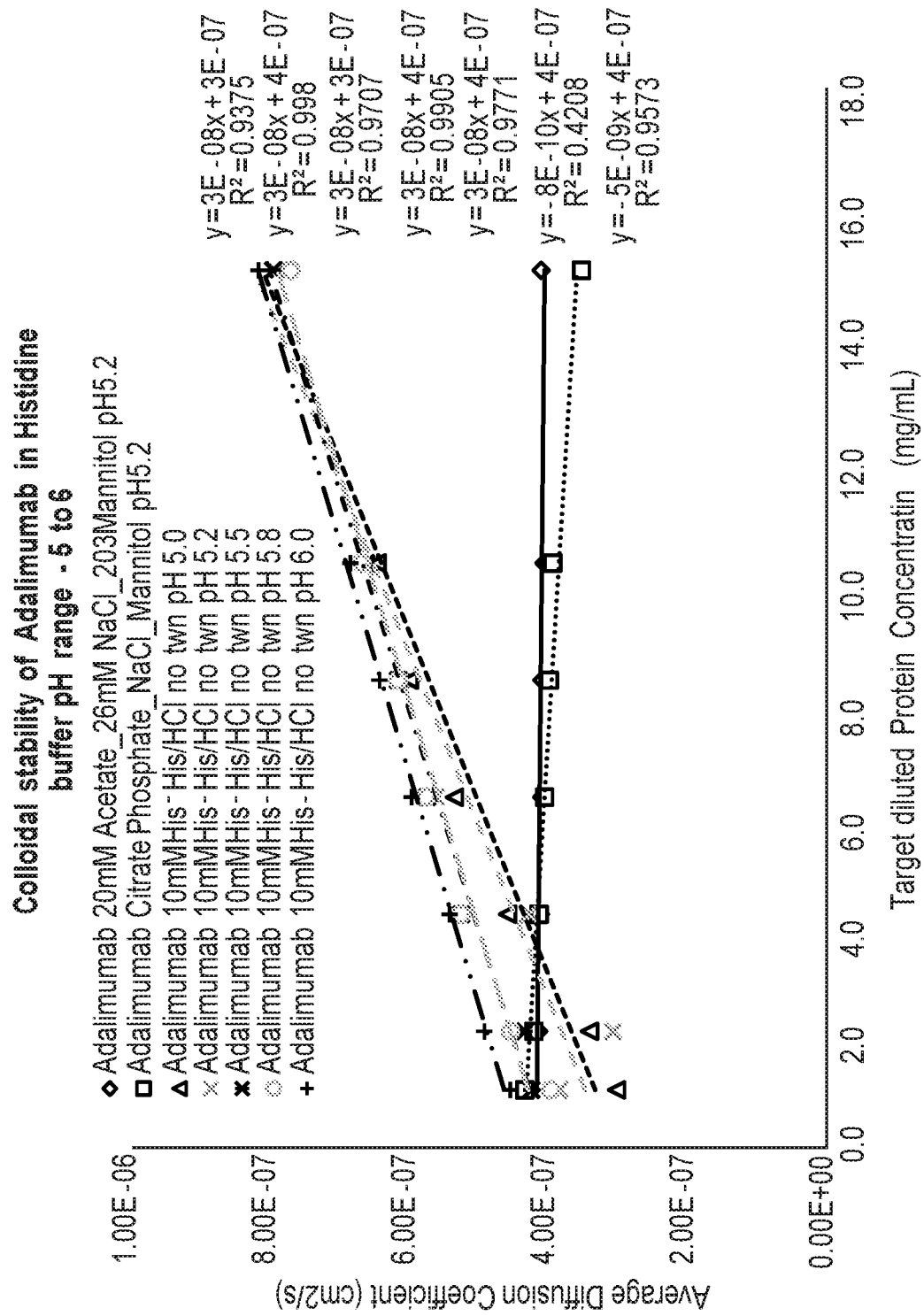
FIG. 21 is a graph depicting the effect of histidine buffer pH range on the colloidal stability of Adalimumab. Histidine buffer having a pH ranging between 5.0 and 6.0.

Colloidal stability of Adalimumab in Histidine buffer is evaluated at varying pH in the range of pH 5 to 6. The findings of the colloidal stability trends are summarized in FIG. 21.

The colloidal stability for Adalimumab as depicted by an increase in average diffusion coefficient remains unchanged in pH range of 5 to 6.

Figure 22:
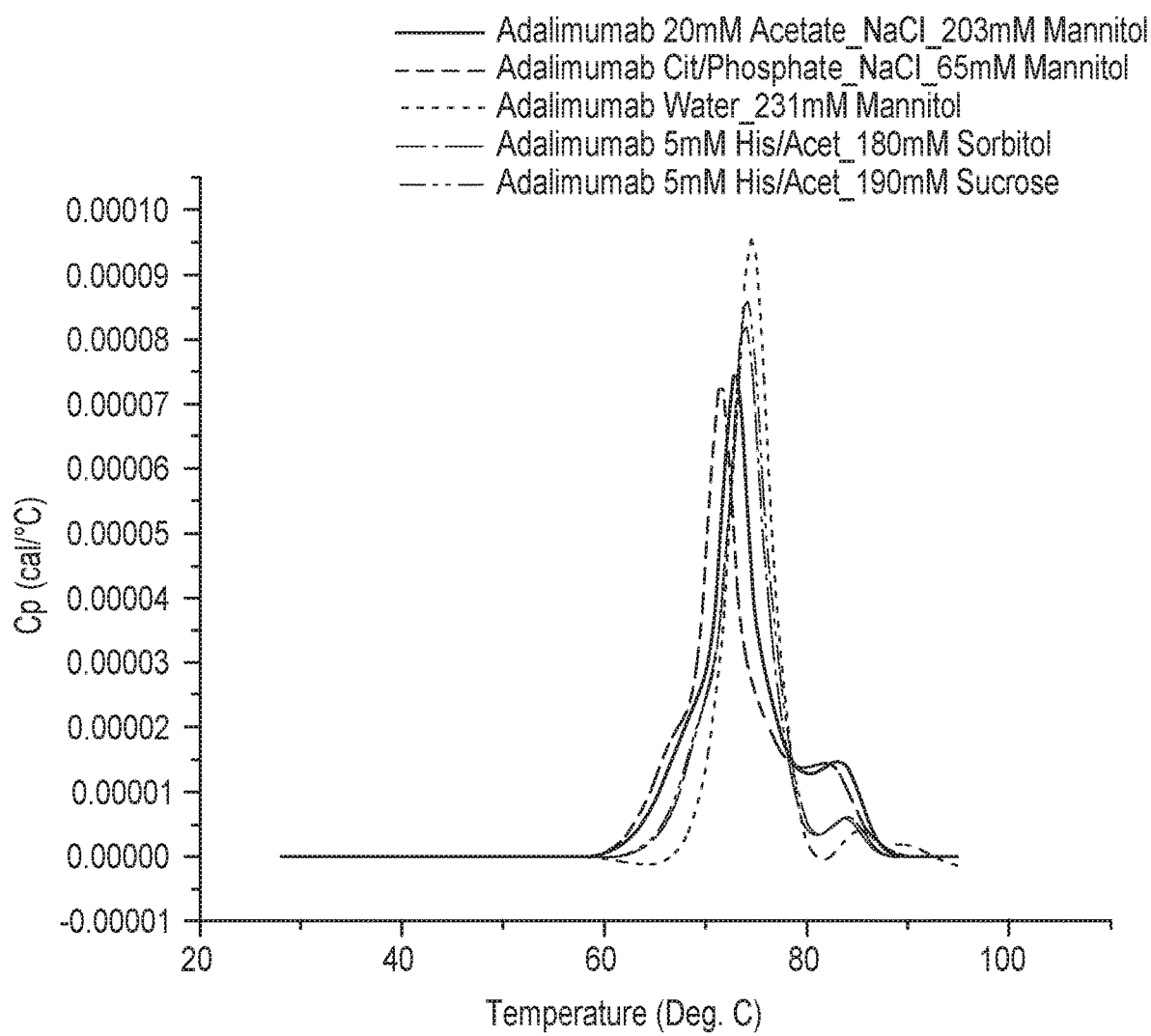
FIG. 22 is a DSC plot depicting a thermal stability profile of Adalimumab in 10 mM histidine-acetate buffer in comparison to alternative buffers.

Conformational and Colloidal Stability of Adalimumab in Histidine-Acetate Buffer:

Conformational stability of Adalimumab in Histidine-Acetate buffer pH 5.2 is compared to that in Histidine buffer, Acetate buffer, citrate-phosphate buffer and water (buffer-less) composition. Two sugars (sucrose, sorbitol) are used as stabilizers with these buffers. The findings of the conformational stability trends are summarized in FIG. 22.

The colloidal stability for Adalimumab in Histidine-Acetate buffer pH 5.2 is greater than that in Histidine buffer pH 5.2 or Acetate buffer pH 5.2 or citrate-phosphate buffer pH 5.2. Also as depicted by the melting temperature (Tm), the conformational stability of Adalimumab in Histidine-Acetate buffer pH 5.2 is equivalent to that in water (buffer-less) composition.

Colloidal stability of Adalimumab in Histidine-Acetate buffer pH 5.2 is compared to that in Histidine buffer and Acetate buffer. 2 sugars (mannitol, sorbitol) are used as stabilizers with these buffers. The findings of the colloidal stability trends are summarized in FIGS. 23 and 24. The colloidal stability for Adalimumab in Histidine-Acetate buffer pH 5.2 is equivalent to that in Histidine buffer pH 5.2 or Acetate buffer pH 5.2.

We claim:

1. A buffered antibody formulation, comprising
   (a) an antibody comprising a heavy chain comprising the amino acid sequence of SEQ ID NO: 1 and a light chain comprising the amino acid sequence of SEQ ID NO: 2;
   (b) a buffer comprising
       (1) 15 mM to 25 mM of an acetate salt,
       (2) 15 mM to 25 mM of histidine and/or a histidine salt,
       (3) 201 mM to 205 mM of sorbitol, and
   (c) 0.08% (v/v) to 0.12% (v/v) of polysorbate 80,
   wherein the antibody formulation has a pH of from 5.1 to 5.3, and
   wherein the formulation comprises from 35 mg to 45 mg of the antibody.

2. The buffered antibody formulation of claim 1, wherein the acetate salt comprises sodium acetate trihydrate.

3. The buffered antibody formulation of claim 1, wherein the pH is 5.2.

4. The buffered antibody formulation of claim 1, wherein the formulation comprises from 37 mg to 43 mg of the antibody.

5. The buffered antibody formulation of claim 1, wherein the formulation comprises 40 mg of the antibody.

6. The buffered antibody formulation of claim 1, wherein the formulation does not comprise NaCl, a citrate, or a phosphate.

7. The buffered antibody formulation of claim 1, wherein the buffer comprises 20 mM of the acetate salt.

8. The buffered antibody formulation of claim 1, wherein the buffer comprises 20 mM of the histidine and/or a histidine salt.

9. The buffered antibody formulation of claim 1, wherein the buffer comprises 203 mM of sorbitol.

10. The buffered antibody formulation of claim 1, wherein the formulation comprises from 0.09% (v/v) to 0.11% (v/v) of polysorbate 80.

11. The buffered antibody formulation of claim 1, wherein the formulation comprises 0.1% (v/v) of polysorbate 80.

12. The buffered antibody formulation of claim 1, wherein the buffer of (b) further comprises from 0.1 to 30 mM of arginine and/or an arginine salt.

13. The buffered antibody formulation of claim 12, wherein the buffer comprises from 10 mM to 30 mM of arginine and/or an arginine salt.

14. The buffered antibody formulation of claim 12, wherein the buffer comprises from 18 mM to 20 mM of arginine and/or an arginine salt.

15. The buffered antibody formulation of claim 12, wherein the buffer comprises 19 mM of arginine and/or an arginine salt.

* * * * *

SEQUENCE LISTING

```
<160> NUMBER OF SEQ ID NOS: 9

<210> SEQ ID NO 1
<211> LENGTH: 451
<212> TYPE: PRT
<213> ORGANISM: Artificial Sequence
<220> FEATURE:
<223> OTHER INFORMATION: Artificial polypeptide

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Artificial polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 121
<212> TYPE: PRT
<213> ORGANISM: Artificial Sequence
<220> FEATURE:
<223> OTHER INFORMATION: Artificial polypeptide

<400> SEQUENCE: 3

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 4

```
<211> LENGTH: 98
<212> TYPE: PRT
<213> ORGANISM: Artificial Sequence
<220> FEATURE:
<223> OTHER INFORMATION: Artificial polypeptide

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 5
<211> LENGTH: 12
<212> TYPE: PRT
<213> ORGANISM: Artificial Sequence
<220> FEATURE:
<223> OTHER INFORMATION: Artificial polypeptide

<400> SEQUENCE: 5

Glu Pro Lys Ser Cys Asp Lys Thr His Thr Cys Pro
1               5                   10

<210> SEQ ID NO 6
<211> LENGTH: 93
<212> TYPE: PRT
<213> ORGANISM: Artificial Sequence
<220> FEATURE:
<223> OTHER INFORMATION: Artificial polypeptide

<400> SEQUENCE: 6

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys
                85                  90

<210> SEQ ID NO 7
<211> LENGTH: 127
<212> TYPE: PRT
<213> ORGANISM: Artificial Sequence
<220> FEATURE:
<223> OTHER INFORMATION: Artificial polypeptide

<400> SEQUENCE: 7
```

Cys Lys Val Ser Asn Lys Ala Leu Pro Ala Pro Ile Glu Lys Thr Ile
1               5                   10                  15

Ser Lys Ala Lys Gly Gln Pro Arg Glu Pro Gln Val Tyr Thr Leu Pro
            20                  25                  30

Pro Ser Arg Asp Glu Leu Thr Lys Asn Gln Val Ser Leu Thr Cys Leu
        35                  40                  45

Val Lys Gly Phe Tyr Pro Ser Asp Ile Ala Val Glu Trp Glu Ser Asn
    50                  55                  60

Gly Gln Pro Glu Asn Asn Tyr Lys Thr Thr Pro Val Leu Asp Ser
65                  70                  75                  80

Asp Gly Ser Phe Phe Leu Tyr Ser Lys Leu Thr Val Asp Lys Ser Arg
                85                  90                  95

Trp Gln Gln Gly Asn Val Phe Ser Cys Ser Val Met His Glu Ala Leu
                100                 105                 110

His Asn His Tyr Thr Gln Lys Ser Leu Ser Leu Ser Pro Gly Lys
            115                 120                 125

<210> SEQ ID NO 8
<211> LENGTH: 108
<212> TYPE: PRT
<213> ORGANISM: Artificial Sequence
<220> FEATURE:
<223> OTHER INFORMATION: Artificial polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg
            100                 105

<210> SEQ ID NO 9
<211> LENGTH: 106
<212> TYPE: PRT
<213> ORGANISM: Artificial Sequence
<220> FEATURE:
<223> OTHER INFORMATION: Artificial polypeptide

<400> SEQUENCE: 9

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

```
His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```